United States Patent [19]
Koepsell et al.

[11] Patent Number: 6,063,623
[45] Date of Patent: May 16, 2000

[54] TRANSPORT PROTEIN WHICH EFFECTS THE TRANSPORT OF CATIONIC XENOBIOTICS AND/OR PHARMACEUTICALS, DNA SEQUENCES ENCODING IT AND THEIR USE

[75] Inventors: Hermann Koepsell, Würzburg; Dirk Gründemann, Heidelberg; Valentin Gorboulev, Würzburg, all of Germany

[73] Assignee: Hoechst Aktiengesellschaft, Frankfurt am Main, Germany

[21] Appl. No.: 08/501,572

[22] Filed: Jul. 12, 1995

[30] Foreign Application Priority Data

Jul. 13, 1994 [DE] Germany .............................. 44 24 577

[51] Int. Cl.$^7$ .......................... C07K 14/435; C12N 5/10; C12N 15/12
[52] U.S. Cl. ........................ 435/371; 435/7.21; 435/69.1; 435/70.3; 435/325; 536/23.5; 536/24.31
[58] Field of Search ................... 435/7.21, 69.1, 435/70.3, 325, 371; 536/23.5, 24.31

[56] References Cited

FOREIGN PATENT DOCUMENTS

WO 93/08261  4/1993  WIPO.

OTHER PUBLICATIONS

Simonson et al. Molecular cloning and characterization of a novel liver–specific transport protein. Journal of Cell Science. vol. 107, pp. 1065–1072, Apr. 1994.

Boerner et al. Polarity of neutral amino acid transport and characterization of a broad specificity transport activity in a kidney epithelial cell line, MDCK. The Journal of Biological Chemistry. vol. 261, No. 30, pp. 13957–13962, Oct. 25, 1986.

Gründemann et al. Drug excretion mediated by a new prototype of polyspecific transporter. Nature. vol. 372, pp. 549–552, Dec. 8, 1994.

Bowie et al. Science 247:1306–1310, 1990.

Wells. Biochemistry 29:8509–8517, 1990.

Ngo et al. The Protein Folding Problem and Tertiary Structure Prediction, Merz et al., eds., Birkhauser, Boston, pp. 492–495, 1994.

Schulz et al. Principles of Protein Structure, Springer–Verlag, New York, pp. 14–16, 1979.

Georges et al. Macromolecular Sequencing and Synthesis: Selected Methods and Applications, Schlesinger, ed., Alan R. Liss, Inc., NY, pp. 127–149, 1988.

Watson et al. Molecular Biology of the Gene, Benjamin/Cummings Publishing Co., Inc., Menlo Park, p. 313, 1987.

*Primary Examiner*—Elizabeth Kemmerer
*Attorney, Agent, or Firm*—Finnegan, Henderson, Farabow, Garrett & Dunner, L.L.P.

[57] ABSTRACT

A transport protein has been cloned which is present in liver epithelial cells and kidney epithelial cells and in intestinal cells and is responsible for transporting cationic pharmaceuticals and/or xenobiotics. This transport protein has been described more specifically by its DNA and amino acid sequences, and various uses are disclosed which are, in particular, of great importance for developing novel medicaments.

22 Claims, 15 Drawing Sheets

FIG. 2a1A

```
  1        GCAGGCCTGGCTAAACTGGTGAGGGCCCTACCCCAGCCATGCCCACCGTGGATGATGTCCT
                                                 MetProThrValAspAspValLeu

61        GGAGCAAGTTGGAGAGTTTGGCCTGGTTCCAGAAACAAGCCTTCCTGTTGCTATGCCTGAT
  9        GluGlnValGlyGluPheGlyLeuValProGluThrSerLeuProValAlaMetProAsp
           GluGlnValGlyGluPheGlyLeuValProGluAsnLysProSerCysTyrAlaCysLeuIle

121        CTCAGCTTCTCTTTAGCTCCCATCTATGTGGCATCGTCTTCCTGGGCTTCACCCCTGGACA
 29        SerAlaSerLeuAlaProIleTyrValGlyIleValPheLeuGlyPheThrProGlyHis

181        TTATTGCCAGAATCCTGGGGTGGCTGAGCTGAGCCAGGGTGGCTGGAGCCAGGCAGA
 49        TyrCysGlnAsnProGlyValAlaGluLeuSerGlnArgCysGlyTrpSerGlnAlaGlu

241        GGAGCTGAACTACACTGTGCCGGGGACCTGTCCGGACCTTCGGAGGACCTCCTTCCTCAGCCA
 69        GluLeuAsnTyrThrValProGlyLeuGlyProSerAspGluAlaSerPheLeuSerGln

301        GTGCATGAGGTATGAGGTGGACTGGAACCAGAGCACCCTGACTGTGTGACCCACTGTC
 89        CysMetArgTyrGluValAspValAspTrpAsnGlnSerThrLeuAspCysValAspProLeuSer

361        CAGCCTGGTTGCCAACAGGAGTCAGTTGCCATTGGGCCCCCTGCCGAGCATGGCTGGGTATA
109        SerLeuValAlaAsnArgSerGlnLeuProLeuGlyProCysGluHisGlyTrpValTyr

421        CGACACTCCCGGCTCCTCCATCGTCACTGAGTTTAACCTGGTGTGTGGAGACGCCTGGAA
129        AspThrProGlySerSerIleValThrGluPheAsnLeuValCysGlyAspAlaTrpLys

481        AGTGGACCTTTTTCAGTCCCTGTGTGAACTTGGGCCTTCTCCTGGCTTCCTGGTTGTGGG
149        ValAspLeuPheGlnSerCysValAsnLeuGlyPheLeuGlySerLeuValValGly

541        TTACATTGCAGACAGGTTTGGCCCTAAGCTCTGTCTCTCTTGGTGACCACGCTGGTCACATC
169        TyrIleAlaAspArgPheGlyArgLysLeuCysLeuLeuValThrThrLeuValThrSer
```

FIG. 2a1B

```
 601  TGTGTCCGGTGTGCTAACAGCGGTGGCCCCAGACTATACATCCATGTTGCTCTTTCGCCT
 189       ValSerGlyValLeuThrAlaValAlaProAspTyrThrSerMetLeuLeuPheArgLeu

661  GCTCAGGGCATGGTCAGCAAGGGCAGCTGGGTGTCCGGCTATACCTTGATCACAGAGTT
 209       LeuGlnGlyMetValSerLysGlySerTrpValSerGlyTyrThrLeuIleThrGluPhe

721  TGTCGGCTCTGGCTACAGGAGAACGACGGCCATTTTGTACCAGATGCCTTCACAGTGGG
 229       ValGlySerGlyTyrArgArgThrThrAlaIleLeuTyrGlnMetAlaPheThrValGly

781  GCTAGTGGGCTTGCCGGGGTGGCCTATGCCATTCCAGACTGGCCTGCTCCAGCTAGC
 249       LeuValGlyLeuAlaGlyLeuValAlaTyrAlaIleProAspTrpArgTrpLeuGlnLeuAla

841  TGTGTCCCTGCCTCACCTTCCTCTGTATTACTGGTTTGTCCCAGAATCCCCCCG
 269       ValSerLeuProThrPheLeuPheLeuLeuTyrLeuTyrTyrTrpPheValProGluSerProArg

901  GTGCCTGTGTCCCAGAAGAACCACGGAGCTGTCAGGATAATGGAGCAAATTGCACA
 289       TrpLeuLeuSerGlnLysArgThrThrArgAlaValArgIleMetGluGlnIleAlaGln

961  GAAGAACGGAAGTGCCTCCTGTGACCTGAAGATGCTCCTGCCTTGAGGAGGATGCCTC
 309       LysAsnGlyLysValProProAlaAspLeuLysMetLeuLeuGluLeuCysLeuGluAspAlaSer

1021  AGAAAAGCGAAGTCCTTCGTTGCCGACCTGTTCCCGACTCCCAACCTGAGGAAGCACAC
 329       GluLysArgSerProSerPheAlaAspLeuPheArgThrProAsnLeuArgLysHisThr

1081  CGTCATCCTGATGTATCTATGGTTCTCTTGTGCTGCTACCAGGGTCTCATCATGCA
 349       ValIleLeuMetTyrLeuTrpPheSerCysAlaValLeuTyrGlnGlyLeuIleMetHis

1141  CGTGGGAGCCACAGGGCCAACCTCTACCTGGACTTCTTTATTCTTCTCTGGTGGAATT
 369       ValGlyAlaThrGlyAlaAsnLeuTyrLeuAspPhePheTyrSerSerLeuValGluPhe
```

FIG. 2a1C

```
1201  CCCCGGGGCCTTCATCATCCTGTCACCATTGACCGCCATTGGCCGCATCTACCCAATAGC
 389  ProAlaAlaPheIleIleIleLeuValThrIleAspArgIleGlyArgIleTyrProIleAla

1261  GGCCTCGAATCTGGTGACGGGGGCAGCCTGCCTCCTCATGATCTTTATCCGCATGAGCT
 409  AlaSerAsnLeuValThrGlyAlaAlaCysLeuLeuMetIleLeuPheIleProHisGluLeu

1321  GCACTGGTGAACGTTACCCTGCCTGTCTTGGCCTGCCTGTCTTGGCCACCATTGTCTGCA
 429  HisTrpLeuAsnValThrLeuAlaCysLeuGlyArgMetGlyAlaThrIleValLeuGlu
                                *

1381  GATGGTCTGCCTGGTGAACGCTGAGCTGTACCCTACATTCATCAGGAATCTTGGGATGAT
 449  MetValCysLeuValAsnAlaGluLeuTyrProThrPheIleArgAsnLeuGlyMetMet

1441  GGTATGCTCTGCCCTGTGTGACCTGGTGGGATCTTCACCCCCTCATGTGTGTTCAGGCT
 469  ValCysSerAlaLeuCysAspLeuProLeuIlePhePheThrProPheMetValPheArgLeu

1501  GATGGAAGTTTGGCAAGCCCTCATTTTGTTTGGGTTTTTGGGCTTGGTGCTGACTGCTGG
 489  MetGluValTrpGlnAlaLeuProLeuIleLeuPheGlyValLeuGlyLeuThrAlaGly

1561  GGCCATGACTCTTCTCCCAGAGACCAAGGTGTGGCCTTGCCTGAGACTATTGAAGA
 509  AlaMetThrLeuLeuLeuProGluThrLysGlyValAlaLeuProGluThrIleGluGlu

1621  AGCAGAGAACCTGGGGAGGAGGAAATCAAAGGCCAAAGAAAACACGATTTACCTTCAGGT
 529  AlaGluAsnLeuGlyArgArgLysSerLysAlaLysThrIleTyrLeuGlnVal

1681  CCAAACAGGCAAGTCCTCAAGTACCTGACAGGGATGCTGTGCCAGGAGCTGAGTGGCAGA
 549  GlnThrGlyLysSerSerThr

1741  GAGAAAGGAGGACTTGGCACTTGGAGGATTCCCAGAAGCCTTTGCCTTTCCAGACTCTTG

1801  TATATATGCACCAGGTTCCAAATGAACTACCAACCTTAAAGACTTTTCTGAAAGCCCAAA

1861  AAAAAAAAAAAAAAAAAAAAAAA
```

FIG. 2a2A

```
          10         20         30         40         50         60
          |          |          |          |          |          |
GAGGGAGACATTGCACCTGGCCACTGCAGCCCAGAGCAGGTCTGGCCACGGCCATGAGCA 70         80         90        100        110        120
          |          |          |          |          |          |
TGCTGAGCCATCATGCCCACCGTGGATGACATTCTGGAGCAGGTTGGGGAGTCTGGCTGG
              METProThrValAspAspIleLeuGluGlnValGlyGluSerGlyTrp 130        140        150        160        170        180
          |          |          |          |          |          |
TTCCAGAAGCAAGCCTTCCTCATCTTATGCCTGCTGTCGGCTGCCTTTGCGCCCATCTGT
PheGlnLysGlnAlaPheLeuIleLeuCysLeuLeuSerAlaAlaPheAlaProIleCys 190        200        210        220        230        240
          |          |          |          |          |          |
GTGGGCATCGTCTTCCTGGGTTTCACACCTGACCACCACTGCCAGAGCCCTGGGGTGGCT
ValGlyIleValPheLeuGlyPheThrProAspHisHisCysGlnSerProGlyValAla 250        260        270        280        290        300
          |          |          |          |          |          |
GAGCTGAGCCAGCGCTGTGGCTGGAGCCCTGCGGAGGAGCTGAACTATACAGTGCCAGGC
GluLeuSerGlnArgCysGlyTrpSerProAlaGluGluLeuAsnTyrThrValProGly 310        320        330        340        350        360
          |          |          |          |          |          |
CTGGGGCCCGCGGGCGAGGCCTTCCTTGGCCAGTGCAGGCGCTATGAAGTGGACTGGAAC
LeuGlyProAlaGlyGluAlaPheLeuGlyGlnCysArgArgTyrGluValAspTrpAsn 370        380        390        400        410        420
          |          |          |          |          |          |
CAGAGCGCCCTCAGCTGTGTAGACCCCCTGGCTAGCCTGGCCACCAACAGGAGCCACCTG
GlnSerAlaLeuSerCysValAspProLeuAlaSerLeuAlaThrAsnArgSerHisLeu 430        440        450        460        470        480
          |          |          |          |          |          |
CCGCTGGGTCCCTGCCAGGATGGCTGGGTGTATGACACGCCCGGCTCTTCCATCGTCACT
ProLeuGlyProCysGlnAspGlyTrpValTyrAspThrProGlySerSerIleValThr 490        500        510        520        530        540
          |          |          |          |          |          |
GAGTTCAACCTGGTGTGTGCTGACTCCTGGAAGCTGGACCTCTTTCAGTCCTGTTTGAAT
GluPheAsnLeuValCysAlaAspSerTrpLysLeuAspLeuPheGlnSerCysLeuAsn 550        560        570        580        590        600
          |          |          |          |          |          |
GCGGGCTTCTTCTTTGGCTCTCTCGGTGTTGGCTACTTTGCAGACAGGTTTGGCCGTAAG
AlaGlyPhePhePheGlySerLeuGlyValGlyTyrPheAlaAspArgPheGlyArgLys
```

FIG. 2a₂B

```
         610       620       630       640       650       660
          |         |         |         |         |         |
CTGTGTCTCCTGGGAACTGTGCTGGTCAACGCGGTGTCGGGCGTGCTCATGGCCTTCTCG
LeuCysLeuLeuGlyThrValLeuValAsnAlaValSerGlyValLeuMETAlaPheSer 670       680       690       700       710       720
          |         |         |         |         |         |
CCCAACTACATGTCCATGCTGCTCTTCCGCCTGCTGCAGGGCCTGGTCAGCAAGGGCAAC
ProAsnTyrMETSerMETLeuLeuPheArgLeuLeuGlnGlyLeuValSerLysGlyAsn 730       740       750       760       770       780
          |         |         |         |         |         |
TGGATGGCTGGCTACACCCTAATCACAGAATTTGTTGGCTCGGGCTCCAGAAGAACGGTG
TrpMETAlaGlyTyrThrLeuIleThrGluPheValGlySerGlySerArgArgThrVal 790       800       810       820       830       840
          |         |         |         |         |         |
GCGATCATGTACCAGATGGCCTTCACGGTGGGGCTGGTGGCGCTTACCGGGCTGGCCTAC
AlaIleMETTyrGlnMETAlaPheThrValGlyLeuValAlaLeuThrGlyLeuAlaTyr 850       860       870       880       890       900
          |         |         |         |         |         |
GCCCTGCCTCACTGGCGCTGGCTGCAGCTGGCAGTCTCCCTGCCCACCTTCCTCTTCCTG
AlaLeuProHisTrpArgTrpLeuGlnLeuAlaValSerLeuProThrPheLeuPheLeu 910       920       930       940       950       960
          |         |         |         |         |         |
CTCTACTACTGGTGTGTGCCGGAGTCCCCTCGGTGGCTGTTATCACAAAAAAGAAACACT
LeuTyrTyrTrpCysValProGluSerProArgTrpLeuLeuSerGlnLysArgAsnThr 970       980       990      1000      1010      1020
          |         |         |         |         |         |
GAAGCAATAAAGATAATGGACCACATCGCTCAAAAGAATGGGAAGTTGCCTCCTGCTGAT
GluAlaIleLysIleMETAspHisIleAlaGlnLysAsnGlyLysLeuProProAlaAsp 1030      1040      1050      1060      1070      1080
          |         |         |         |         |         |
TTAAAGATGCTTTCCCTCGAAGAGGATGTCACCGAAAAGCTGAGCCCTTCATTTGCAGAC
LeuLysMETLeuSerLeuGluGluAspValThrGluLysLeuSerProSerPheAlaAsp 1090      1100      1110      1120      1130      1140
          |         |         |         |         |         |
CTGTTCCGCACGCCGCGCCTGAGGAAGCGCACCTTCATCCTGATGTACCTGTGGTTCACG
LeuPheArgThrProArgLeuArgLysArgThrPheIleLeuMETTyrLeuTrpPheThr 1150      1160      1170      1180      1190      1200
          |         |         |         |         |         |
GACTCTGTGCTCTATCAGGGGCTCATCCTGCACATGGGCGCCACCAGCGGGAACCTCTAC
AspSerValLeuTyrGlnGlyLeuIleLeuHisMETGlyAlaThrSerGlyAsnLeuTyr 1210      1220      1230      1240      1250      1260
          |         |         |         |         |         |
CTGGATTTCCTTTACTCCGCTCTGGTCGAAATCCCGGGGGCCTTCATAGCCCTCATCACC
LeuAspPheLeuTyrSerAlaLeuValGluIleProGlyAlaPheIleAlaLeuIleThr
```

FIG. 2a2C

```
           1270      1280      1290      1300      1310      1320
             |         |         |         |         |         |
ATTGACCGCGTGGGCCGCATCTACCCCATGGCCGTGTCAAATTTGTTGGCGGGGGCAGCC
IleAspArgValGlyArgIleTyrProMETAlaValSerAsnLeuLeuAlaGlyAlaAla 1330      1340      1350      1360      1370      1380
             |         |         |         |         |         |
TGCCTCGTCATTTTTATCTCACCTGACCTGCACTGGTTAAACATCATAATCATGTGTGTT
CysLeuValIlePheIleSerProAspLeuHisTrpLeuAsnIleIleIleMETCysVal 1390      1400      1410      1420      1430      1440
             |         |         |         |         |         |
GGCCGAATGGGAATCACCATTGCAATACAAATGATCTGCCTGGTGAATGCTGAGCTGTAC
GlyArgMETGlyIleThrIleAlaIleGlnMETIleCysLeuValAsnAlaGluLeuTyr 1450      1460      1470      1480      1490      1500
             |         |         |         |         |         |
CCCACATTCGTCAGGAACCTCAGAGTGATGGTGTGTTCCTCCCTGTGTGACATAGGTGGG
ProThrPheValArgAsnLeuArgValMETValCysSerSerLeuCysAspIleGlyGly 1510      1520      1530      1540      1550      1560
             |         |         |         |         |         |
ATAATCACCCCCTTCATAGTCTTCAGGCTGAGGGAGGTCTGGCAAGCCTTGCCCCTCATT
IleIleThrProPheIleValPheArgLeuArgGluValTrpGlnAlaLeuProLeuIle 1570      1580      1590      1600      1610      1620
             |         |         |         |         |         |
TTGTTTGCGGTGTTGGGCCTGCTTGCCGCGGGAGTGACGCTACTTCTTCCAGAGACCAAG
LeuPheAlaValLeuGlyLeuLeuAlaAlaGlyValThrLeuLeuLeuProGluThrLys 1630      1640      1650      1660      1670      1680
             |         |         |         |         |         |
GGGGACGCTTTGCCAGAGACCATGAAGGACGCCGAGAACCTTGGGAGAAAAGCAAAGCCC
GlyAspAlaLeuProGluThrMETLysAspAlaGluAsnLeuGlyArgLysAlaLysPro 1690      1700      1710      1720      1730      1740
             |         |         |         |         |         |
AAAGAAAACACGATTTACCTTAAGGTCCAAACCTCAGAACCCTCGGGCACCTGAGAGAGA
LysGluAsnThrIleTyrLeuLysValGlnThrSerGluProSerGlyThr 1750      1760      1770      1780      1790      1800
             |         |         |         |         |         |
TGTTTTGCGGCGATGTCGTGTTGGAGGGATGAAGATGGAGTTATCCTCTGCAGAAATTCC 1810      1820      1830      1840      1850      1860
             |         |         |         |         |         |
TAGACGCCTTCACTTCTCTGTATTCTTCCTCATACTTGCCTACCCCAAATTAATATCAG 1870      1880
             |         |
TCCTAAAGAAAAAAAAAAAAAAAAA
```

FIG. 2a3A

```
            10         20         30         40         50         60
            |          |          |          |          |          |
GGCCCTGCCCTGAAGGCTGGTCACTTGCAGAGGTAAACTCCCCTCTTTGACTTCTGGCCA 70         80         90        100        110        120
            |          |          |          |          |          |
GGGTTTGTGCTGAGCTGGCTGCAGCCGCTCTCAGCCTCGCTCCGGGCACGTCGGGCAGCC 130        140        150        160        170        180
            |          |          |          |          |          |
TCGGGCCCTCCTGCCTGCAGGATCATGCCCACCACCGTGGACGATGTCCTGGAGCATGGA
                            METProThrThrValAspAspValLeuGluHisGly 190        200        210        220        230        240
            |          |          |          |          |          |
GGGGAGTTTCACTTTTTCCAGAAGCAAATGTTTTTCCTCTTGGCTCTGCTCTCGGCTACC
GlyGluPheHisPhePheGlnLysGlnMETPhePheLeuLeuAlaLeuLeuSerAlaThr 250        260        270        280        290        300
            |          |          |          |          |          |
TTCGCGCCCATCTACGTGGGCATCGTCTTCCTGGGCTTCACCCCTGACCACCGCTGCCGG
PheAlaProIleTyrValGlyIleValPheLeuGlyPheThrProAspHisArgCysArg 310        320        330        340        350        360
            |          |          |          |          |          |
AGCCCCGGAGTGGCCGAGCTGAGTCTGCGCTGCGGCTGGAGTCCTGCAGAGGAACTGAAC
SerProGlyValAlaGluLeuSerLeuArgCysGlyTrpSerProAlaGluGluLeuAsn 370        380        390        400        410        420
            |          |          |          |          |          |
TACACGGTGCCGGGCCCAGGACCTGCGGGCGAAGCCTCCCCAAGACAGTGTAGGCGCTAC
TyrThrValProGlyProGlyProAlaGlyGluAlaSerProArgGlnCysArgArgTyr 430        440        450        460        470        480
            |          |          |          |          |          |
GAGGTGGACTGGAACCAGAGCACCTTTGACTGCGTGGACCCCCTGGCCAGCCTGGACACC
GluValAspTrpAsnGlnSerThrPheAspCysValAspProLeuAlaSerLeuAspThr 490        500        510        520        530        540
            |          |          |          |          |          |
AACAGGAGCCGCCTGCCACTGGGCCCCTGCCGGGACGGCTGGGTGTACGAGACGCCTGGC
AsnArgSerArgLeuProLeuGlyProCysArgAspGlyTrpValTyrGluThrProGly 550        560        570        580        590        600
            |          |          |          |          |          |
TCGTCCATCGTCACCGAGTTTAACCTGGTATGTGCCAACTCCTGGATGTTGGACCTATTC
SerSerIleValThrGluPheAsnLeuValCysAlaAsnSerTrpMETLeuAspLeuPhe
```

FIG. 2a₃B

```
          610        620        630        640        650        660
           |          |          |          |          |          |
CAGTCATCAGTGAATGTAGGATTCTTTATTGGCTCTATGAGTATCGGCTACATAGCAGAC
GlnSerSerValAsnValGlyPhePheIleGlySerMETSerIleGlyTyrIleAlaAsp 670        680        690        700        710        720
           |          |          |          |          |          |
AGGTTTGGCCGTAAGCTCTGCCTCCTAACTACAGTCCTCATAAATGCTGCAGCTGGAGTT
ArgPheGlyArgLysLeuCysLeuLeuThrThrValLeuIleAsnAlaAlaAlaGlyVal 730        740        750        760        770        780
           |          |          |          |          |          |
CTCATGGCCATTTCCCCAACCTATACGTGGATGTTAATTTTTCGCTTAATCCAAGGACTG
LeuMETAlaIleSerProThrTyrThrTrpMETLeuIlePheArgLeuIleGlnGlyLeu 790        800        810        820        830        840
           |          |          |          |          |          |
GTCAGCAAAGCAGGCTGGTTAATAGGCTACATCCTGATTACAGAATTTGTTGGGGGGAGA
ValSerLysAlaGlyTrpLeuIleGlyTyrIleLeuIleThrGluPheValGlyGlyArg 850        860        870        880        890        900
           |          |          |          |          |          |
TATCGGAGAACAGTGGGGATTTTTTACCAAGTTGCCTATACAGTTGGGCTCCTGGTGCTA
TyrArgArgThrValGlyIlePheTyrGlnValAlaTyrThrValGlyLeuLeuValLeu 910        920        930        940        950        960
           |          |          |          |          |          |
GCTGGGGTGGCTTACGCACTTCCTCACTGGAGGTGGTTGCAGTTCACAGTTGCTCTGCCC
AlaGlyValAlaTyrAlaLeuProHisTrpArgTrpLeuGlnPheThrValAlaLeuPro 970        980        990       1000       1010       1020
           |          |          |          |          |          |
AACTTCTTCTTCTTGCTCTATTACTGGTGCATACCTGAGTCTCCCAGGTGGCTGATCTCC
AsnPhePhePheLeuLeuTyrTyrTrpCysIleProGluSerProArgTrpLeuIleSer 1030       1040       1050       1060       1070       1080
           |          |          |          |          |          |
CAGAATAAGAATGCTGAAGCCATGAGAATCATTAAGCACATCGCAAAGAAAAATGGAAAA
GlnAsnLysAsnAlaGluAlaMETArgIleIleLysHisIleAlaLysLysAsnGlyLys 1090       1100       1110       1120       1130       1140
           |          |          |          |          |          |
TCTCTACCCGCCTCCCTTCAGCGCCTGAGACTTGAAGAGGAAACTGGCAAGAAATTGAAC
SerLeuProAlaSerLeuGlnArgLeuArgLeuGluGluGluThrGlyLysLysLeuAsn 1150       1160       1170       1180       1190       1200
           |          |          |          |          |          |
CCTTCATTTCTTGACTTGGTCAGAACTCCTCAGATAAGGAAACATACTATGATATTGATG
ProSerPheLeuAspLeuValArgThrProGlnIleArgLysHisThrMETIleLeuMET 1210       1220       1230       1240       1250       1260
           |          |          |          |          |          |
TACAACTGGTTCACGAGCTCTGTGCTCTACCAGGGCCTCATCATGCACATGGGCCTTGCA
TyrAsnTrpPheThrSerSerValLeuTyrGlnGlyLeuIleMETHisMETGlyLeuAla
```

FIG. 2a3C

```
          1270      1280      1290      1300      1310      1320
            |         |         |         |         |         |
GGTGACAATATCTACCTGGATTTCTTCTACTCTGCCCTGGTTGAATTCCCAGCTGCCTTC
GlyAspAsnIleTyrLeuAspPhePheTyrSerAlaLeuValGluPheProAlaAlaPhe 1330      1340      1350      1360      1370      1380
            |         |         |         |         |         |
ATGATCATCCTCATTATCGACCGCATCGGACGCCGTTACCCTTGGGCTGCATCAAATATG
METIleIleLeuIleIleAspArgIleGlyArgArgTyrProTrpAlaAlaSerAsnMET 1390      1400      1410      1420      1430      1440
            |         |         |         |         |         |
GTTGCAGGGGCAGCCTGTCTGGCCTCAGTTTTTATACCTGGTGATCTACAATGGCTAAAA
ValAlaGlyAlaAlaCysLeuAlaSerValPheIleProGlyAspLeuGlnTrpLeuLys 1450      1460      1470      1480      1490      1500
            |         |         |         |         |         |
ATTATTATCTCATGCTTGGGAAGAATGGGGATCACAATGGCCTATGAGATAGTCTGCCTG
IleIleIleSerCysLeuGlyArgMETGlyIleThrMETAlaTyrGluIleValCysLeu 1510      1520      1530      1540      1550      1560
            |         |         |         |         |         |
GTCAATGCTGAGCTGTACCCCACATTCATTAGGAATCTTGGCGTCCACATCTGTTCCTCA
ValAsnAlaGluLeuTyrProThrPheIleArgAsnLeuGlyValHisIleCysSerSer 1570      1580      1590      1600      1610      1620
            |         |         |         |         |         |
ATGTGTGACATTGGTGGCATCATCACGCCATTCCTGGTCTACCGGCTCACTAACATCTGG
METCysAspIleGlyGlyIleIleThrProPheLeuValTyrArgLeuThrAsnIleTrp 1630      1640      1650      1660      1670      1680
            |         |         |         |         |         |
CTTGAGCTCCCGCTGATGGTTTTCGGCGTACTTGGCTTGGTTGCTGGAGGTCTGGTGCTG
LeuGluLeuProLeuMETValPheGlyValLeuGlyLeuValAlaGlyGlyLeuValLeu 1690      1700      1710      1720      1730      1740
            |         |         |         |         |         |
TTGCTTCCAGAAACTAAAGGGAAAGCTTTGCCTGAGACCATCGAGGAAGCCGAAAATATG
LeuLeuProGluThrLysGlyLysAlaLeuProGluThrIleGluGluAlaGluAsnMET 1750      1760      1770      1780      1790      1800
            !         !         !         !         !         !
CAAAGACCAAGAAAAAATAAAGAAAAGATGATTTACCTCCAAGTTCAGAAACTAGACATT
GlnArgProArgLysAsnLysGluLysMETIleTyrLeuGlnValGlnLysLeuAspIle 1810      1820      1830      1840      1850      1860
            !         !         !         !         !         !
CCATTGAACTAAGAAGAGAGACCGTTGCTGCTGTCATGACCTAGCTTTATGGCAGCAAGA
ProLeuAsn 1870      1880      1890
            !         !         !
CCAAAAGTAGAAATCCCTGCACTCATCACAAAGCCC
```

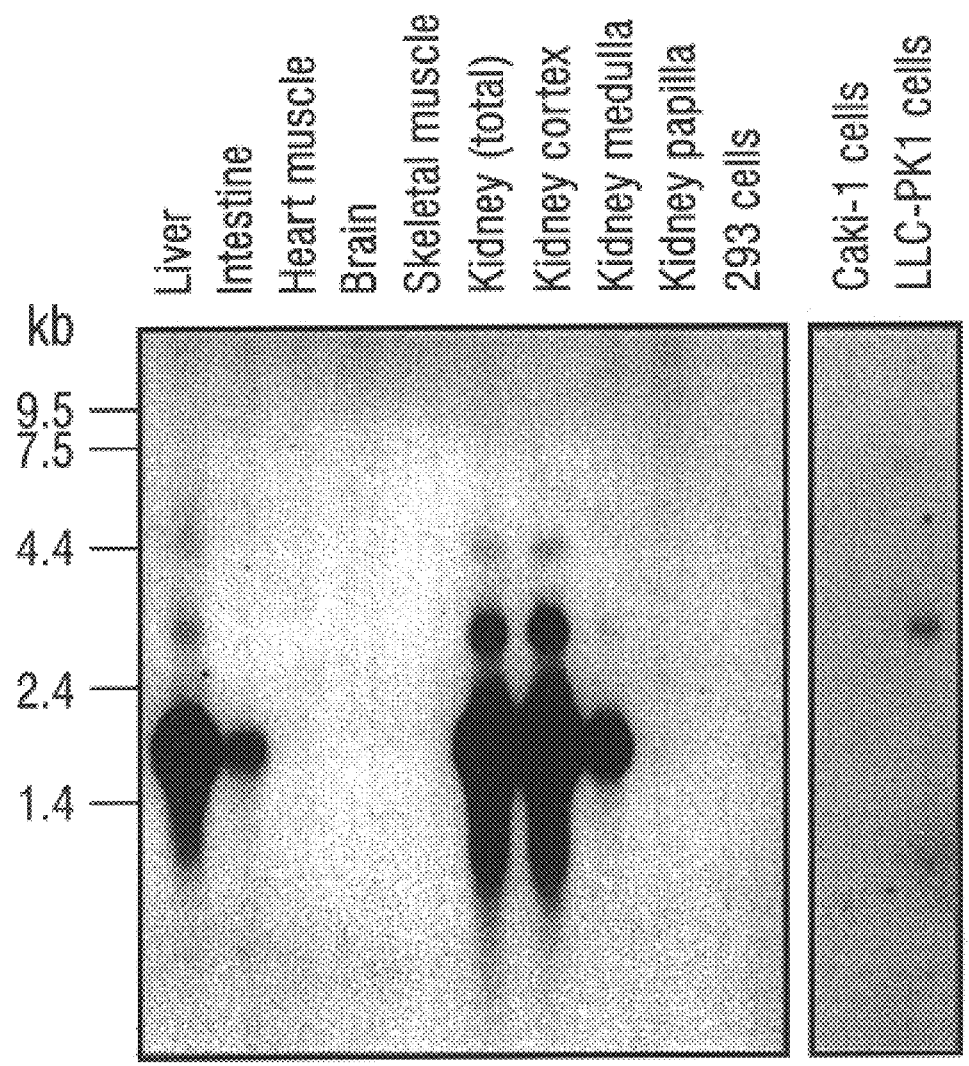

TRANSPORT PROTEIN WHICH EFFECTS THE TRANSPORT OF CATIONIC XENOBIOTICS AND/OR PHARMACEUTICALS, DNA SEQUENCES ENCODING IT AND THEIR USE

BACKGROUND OF THE INVENTION

In mammals, and in humans in particular, cationic pharmaceuticals and xenobiotics of varying molecular structure, catecholamines and other endogenous cations are excreted in the kidney and liver by polyspecific transport proteins which are located in luminal and basolateral plasma membranes. These transport proteins differ, as regards their function, from the previously known monoamine transport proteins in neuronal plasma membranes and synaptic vesicles and from the ATP-dependent proteins for exporting hydrophobic pharmaceuticals (multidrug transport proteins).

Within the scope of the present invention, a complementary DNA sequence was initially isolated from rat kidneys, which sequence encodes a membrane protein of 556 amino acids in length and is designated OCT1 in that which follows. This transport protein acts in the basolateral membrane of the proximal renal tubules and in hepatocytes as a cation transporter for various target molecules.

The transport protein designated OCT1 is not homologous with any other previously known protein, exhibits a thus far unique distribution of hydrophobic and negatively charged amino acids and is found exclusively in kidneys, the liver and intestine. The OCT1 transport protein transports cations of varying structure, is inhibited by a large number of cationic substances of differing hydrophobicity and possesses functional properties which differ from those of a previously known polyspecific transport protein (multidrug transporter), which is only able to transport very hydrophobic substances. The transport protein OCT1 is regarded as a new prototype of a polyspecific transport protein in mammals.

Many organic cations, including frequently used pharmaceuticals such as antihistamines, antiarrhythmics, sedatives, opiates, diuretics, cytostatic agents and antibiotics, are excreted into the urine and into the bile by means of being actively transported through kidney epithelial cells and hepatocytes. When being actively secreted in the kidney, the cations are transported by polyspecific transport systems in the basolateral and luminal plasma membranes of the proximal renal tubules. The two systems differ as regards their function. The transport proteins in the basolateral membrane, which are able to transport structurally different cations such as tetraethylanmonium (TEA), $N^1$-methylnicotinamide (NMN) and N-methyl-4-phenylpyridinium (MPP), are inhibited by a large number of extracellular cations of differing structure. These transport proteins can be driven by a membrane potential which is internally negative and by the oppositely directed transport of intracellular substrates. Two transport systems have been described in the luminal membrane which, while being driven by an outwardly directed proton gradient, are not affected by the membrane potential. One of these transport systems has a broad substrate specificity which is comparable to that of the cation transport system in the basolateral membrane of proximal renal tubules. Owing to functional similarities, it is assumed that this polyspecific transport system in the luminal membrane is identical to the extraneuronal transport system for noradrenalin in the heart.

SUMMARY OF THE INVENTION

The present invention therefore relates to transport proteins which are responsible for transporting cationic xenobiotics and/or pharmaceuticals from the blood into the epithelial cells of the liver or kidney or for transporting cationic xenobiotics or pharmaceuticals from the intestine into the blood circulation.

The novel transport proteins exhibit a constituent sequence of at least seven amino acids selected from the amino acid sequence which is depicted in FIG. $2a_1$A–C (SEQ ID NO.1), FIG. $2a_2$A–C, (SEQ ID NO.2) or FIG. $2a_3$A–C (SEQ ID NO.3). In a preferred embodiment, the constituent sequence from FIG. $2a_1$A–C (SEQ ID NO.1), FIG. $2a_2$A–C or FIG. $2a_3$A–C (SEQ ID NO.3) has a length of at least 10 amino acids and, in a particularly preferred embodiment, a length of at least 14 amino acids.

The present invention also relates to DNA sequences which encode a novel transport protein. The novel DNA sequences exhibit a constituent sequence of at least 21 bases selected from the sequence shown in FIG. $2a_1$A–C (SEQ ID NO.4), $2a_2$A–C (SEQ ID NO.5) or $2a_3$A–C (SEQ ID NO.6). In a particularly preferred embodiment, the constituent sequence has a length of at least 30 bases and, in a very particularly preferred embodiment, of at least 42 bases.

The novel transport proteins and DNA sequences are of particular importance in medical and pharmacological research. The novel DNA sequences can be used, for example, to prepare epithelial cell lines which permanently express a novel transport protein. For this purpose, the DNA sequence encoding the transport protein is incorporated, using genetic manipulation methods which are known per se, into a suitable vector, which is used to transform a suitable epithelial cell line which did not previously express the transport protein. In this way, cell lines can be obtained which constantly express a novel transport protein.

Epithelial cell lines of this nature, which express the transport proteins, can be employed in vitro to test the renal and biliary excretion, and also the intestinal absorption, of cationic pharmaceuticals and/or xenobiotics which are to be expected. Thus, such cell lines can be used to determine at the in vitro stage, that is without elaborate animal experiments, whether and if so to what extent pharmaceuticals, and other biologically active compounds as well, are excreted or absorbed from the intestine into the blood circulation.

The novel DNA sequences can be used to isolate those transport proteins which are homologous with the novel transport proteins. The corresponding transport proteins which are homologous with the transport proteins disclosed in accordance with the invention can therefore be isolated from all mammalian species and from humans. Two corresponding human sequences have already been determined. One possible means of effecting such an isolation is to use the now well known polymerase chain reaction. To do this, it is only necessary to select suitable DNA sequences from the sequence shown in FIG. $2a_1$A–C (SEQ ID NO.4), $2a_2$A–C (SEQ ID NO:5) or $2a_3$A–C (SEQ ID NO.6) which can serve as primers for the polymerase chain reaction. These primers can be used to isolate homologous transport proteins without difficulty.

A further possible use of the novel transport proteins and/or of the novel epithelial cell lines is to develop cationic signal molecules which can be attached to biologically active compounds, such as pharmaceuticals, in order to alter their renal and biliary excretion or their intestinal absorption. In this way it is possible to examine different chemical structures to see whether they favor excretion via the kidney or the liver of the molecule to which they are linked, and also promote absorption from the intestine into the blood circulation, or whether they bring about the opposite effect in each case.

The novel transport proteins can also be employed, in particular, for generating antibodies, in particular monoclonal antibodies, which can be used to block the uptake of pharmaceuticals into renal tubule cells in order to decrease the nephrotoxicity of cationic pharmaceuticals.

Furthermore, the disclosure of the invention can be used as the basis for developing specific pharmaceuticals which affect the excretion of certain other cationic pharmaceuticals and/or xenobiotics. In this way it is possible to develop pharmacologically active substances which are able to influence the uptake of other active compounds. An influence of this nature can either comprise promoting or preventing uptake of an active compound from the intestine or promoting or preventing excretion of an active compound in the kidney and liver.

An additional preferred use of the novel DNA sequences is that of developing antisense nucleotide sequences. In this context, nucleotide sequences can be developed which prevent transcription and/or translation of the corresponding genes by binding to the corresponding, naturally occurring, complementary nucleotide sequences.

An additional preferred use of the novel DNA sequences is their use in molecular test kits for diagnosing molecular defects at the genome level in renal and/or biliary cation excretion mechanisms. In molecular test kits of this nature, the DNA sequences can be used, in a particularly preferred embodiment, for carrying out the polymerase chain reaction. In this case, the known DNA sequence is used as the basis for selecting and synthesizing primer sequences which can then be employed in the polymerase chain reaction to amplify the gene from the respective patient which encodes the cation transporter and to examine this gene for genetic mutations.

DETAILED DESCRIPTION OF THE INVENTION

The nature of the present invention is explained in more detail with the aid of the following examples which are not, however, intended to limit the invention.

EXAMPLE 1

In order to clone the genes encoding the transport protein, blunt-ended double-stranded cDNA was firstly prepared from rat kidney poly(A)$^+$ RNA using a NotI oligo(dT) primer for synthesizing the first strand. Once EcoRI adaptors containing an SP6 RNA polymerase promoter had been attached to the cDNA, the latter was digested with NotI and the resulting fragments were size-fractionated (1.5 to 2.3 kb) and inserted into the EcoRI restriction site of the vector pBluescript (Stratagene); the recombinant vector was then electroporated into the E.coli strain DH10B. The plasmid DNA was isolated from pools of transformants, linearized with NotI and transcribed using the SP6 RNA polymerase. The cRNA was purified by means of poly(A)$^+$ selection and injected at a concentration of from 20 to 40 ng per oocyte. The oocytes were incubated and the NMN-inhibitable $^{14}$C-TEA uptake was measured. Using a targeted screening method, a single clone, containing the gene encoding a kidney cation transporter, was isolated from the gene library. It was only possible to isolate this clone after having optimized and partially modified the methods which were used. In order to sequence the identified DNA, overlapping restriction fragments of OCT1 were subcloned and completely sequenced on both strands.

The OCT1 gene, which was isolated from a rat kidney gene bank and which comprised a cDNA fragment of 1882 base pairs in length, was expressed in Xenopus laevis oocytes. For this purpose, the oocytes were incubated, following RNA injection, for three days in 5 mM Hepes-Tris buffer, pH 7.5, 110 mM NaCl, 3 mM KCl, 2 mM CaCl$_2$, 1 mM MgCl$_2$ (designated ORi in that which follows). Transport was measured by incubating the oocytes with $^{14}$C-TEA (tetraethylammonium) which was dissolved in ORi (22° C.). Furthermore, experiments were carried out using differing concentrations of Na$^+$ and K$^+$, as were experiments in the presence of Ba$^{++}$, at different pH values and in the presence of different inhibitors. Since, at the $^{14}$C-TEA concentrations used, the uptake brought about by expressed OCT1 protein was linear in ORi buffer for more than 90 minutes, the uptake rates were determined after 90 minutes of incubation. When measurements were made with altered concentrations of Na$^+$, K$^+$ and H$^+$ and in the presence of inhibitors, the oocytes were firstly incubated for 30 minutes under the appropriate buffer conditions and the uptake rates were then determined during a 30-minute period of incubation with $^{14}$C-TEA. Following the incubation with $^{14}$C-TEA, the uptake was terminated and the oocytes were washed and examined for the amount of radioactivity they had taken up.

Thus, the 1882 base pair cDNA fragment was expressed using Xenopus laevis oocytes (as described above); the OCT1 protein which was expressed in this way induced an uptake of $^{14}$C-tetraethylammonium ($^{14}$C-TEA) which NMN (N$^1$-methylnicotinamide) was able to inhibit, with the uptake being more than 250 times the values obtained in controls in which the oocytes were injected with water. The results are depicted graphically in FIG. 1a.

The cloned OCT1 cDNA contains an open reading frame which encodes a membrane protein having 556 amino acids. The amino acid sequence is depicted in FIG. 2$a_1$A–C (SEQ ID NO.1). It exhibits no similarities to the proteins in data banks.

The expression of $^{14}$C-TEA uptake depended on the quantity of OCT1 cRNA that was injected. These results are presented in FIG. 1b. The cRNA-dependence of the expressed uptake could be described by the Hill equation in which n=approximately 2.

The substance dependence of the $^{14}$C-TEA uptake elicited by the OCT1 transport protein followed the Michaelis Menten equation. These results are depicted in FIG. 1c. The estimated K$_m$ value of 95±$\mu$M was similar to the K$_m$ value (160 $\mu$M) for cation transport through the basolateral membrane of rat proximal renal tubules which was determined in earlier experiments. It was 14 times lower than the apparent K$_m$ value for the polyspecific H$^+$ cation antiporter in the brush border membrane of rat proximal renal tubules.

EXAMPLE 2

In order to establish, in addition, whether the OCT1 transport protein represented the potential-dependent polyspecific cation transport system from the basolateral membrane or the potential-independent polyspecific H$^+$ cation antiport system of the brush border membrane, tests were carried out to determine whether the uptake elicited by the OCT1 transport protein was dependent on the membrane potential or on a protein gradient across the membrane. The ability of different inhibitors to inhibit the expressed $^{14}$C-TEA uptake was also investigated.

FIGS. 1d and 1e demonstrate that while the uptake of $^{14}$C-TEA mediated by the OCT1 transport protein is dependent on the membrane potential, it is not altered appreciably when an inwardly directed or outwardly directed proton gradient of one pH unit is applied. The OCT1 transport protein therefore has the same basic characteristics as the cation transport measured across the basolateral membrane of the proximal renal tubules.

FIG. 1f and Table 1 demonstrate that the uptake of $^{14}$C-TEA brought about by OCT1 is inhibited by organic cations of differing molecular structure. These structures include several frequently used pharmaceuticals such as quinine, desipramine, procainamide and O-methylisoprenaline. The estimated $K_i$ values lie between 0.13 µM for 1-ethyl-2([1,4-dimethyl-2-phenyl-6-pyrimidinylidene]-methyl)quinolinium chloride (cyanin 863) and 1 mM for tetramethylammonium (TMA).

TABLE 1

| Inhibitor | $K_i$ (µM) |
| --- | --- |
| Cyanine 863 | 0.13 ± 0.02 |
| Decynium 22 | 0.36 ± 0.08 |
| Tetrapentylammonium | 0.43 ± 0.09 |
| Quinine | 0.93 ± 0.08 |
| Desipramine | 2.8 ± 0.6 |
| Mepiperphenidol | 5.2 ± 0.3 |
| Procainamide | 13 ± 2 |
| 1-Methyl-4-phenylpyridinium | 13 ± 2 |
| Corticosterone | >10 |
| Reserpine | >20 |
| O-Methylieoprenaiine | 43 ± 5 |
| Tetramethylammonium | 1000 ± 100 |
| $N^1$-Methylnicotinamide | 1000 ± 200 |

Table 1 shows the sensitivity of $^{14}$C-TEA uptake in Xenopus laevis oocytes which were injected with the cRNA of the OCT1 renal transport protein.

When carrying out the inhibition experiments, the Xenopus laevis oocytes were injected with 5 ng of OCT1 cRNA and the effects of from 5 to 8 different concentrations of the inhibitors listed in Table 1 on the 95 µM uptake into the oocytes were measured. The values were also given in FIG. 1f. The inhibition curves were fitted by nonlinear regression analysis and the $K_i$ values (±SD) were determined.

In contrast to the previously known polyspecific transport protein, the so-called multidrug transporter, which is only inhibited by hydrophobic substances, the novel OCT1 transport protein was also inhibited by hydrophilic compounds such as TMA and NMN. Desipramine inhibited the transport elicited by OCT1 with a $K_i$ value which was 700 fold greater than that with which it inhibited neuronal noradrenalin transport in plasma membranes of nerve cells. 5 µM reserpine has no effect on OCT1-elicited transport whereas the neuronal monoamine transport protein in synaptic vesicles is inhibited by subnanomolar concentrations of reserpine.

EXAMPLE 3

It was possible to confirm that the OCT1 transport protein was identical to the basolateral cationic transport protein by comparing the OCT1 $K_i$ values with functional data which had previously been obtained from membrane vesicles and from measurements using cultured kidney epithelial cells. In making such a comparison, consideration has to be given to the species-dependent differences in cation transport and to the methodological limitations of the different methods for measuring inhibition of cation transport. In previous investigations, cation transport in rat kidneys was determined by microperfusion experiments which have to be carried out using short incubation times (4 seconds). Since it is not possible to use this method to determine diffusion-independent $K_i$ values for high-affinity inhibitors, we have restricted ourselves to comparing low-affinity inhibitors. In a comparison of the low-affinity inhibitors TMA and NMN, we found that the $K_i$ values for the OCT1-expressed transport protein (approximately 1 mM) correspond to the $K_i$ values (TMA 1.4 mM and NMN 0.54 mM) which were measured for the basolateral uptake of TEA into rat proximal renal tubules. They clearly differ from the $K_i$ values (TMA 70 mM and NMN 8.3 mM) which were determined for the luminal uptake of TEA.

EXAMPLE 4

Additional support for the basolateral location of OCT1 is provided by the $K_i$ value (0.4 µM) which was obtained for the inhibition of OCT1-elicited uptake by 1,1'-diethyl-2,2'-cyanine iodide (decynium 22). In LLC-PK1 cells, a $K_i$ value of 5.6 nM was determined for the transport of TEA across the luminal membrane whereas the $K_i$ value for the transport of TEA across the basolateral membrane was estimated to be >0.1 µM. In order to characterize the OCT1 transport protein further, tests were carried out to determine whether MPP, which has an approximately 10 fold greater affinity than does TEA, is likewise transported by OCT1. Following the injection of 8 ng of OCT1 cRNA into oocytes, a specific uptake of $^3$H-MPP was expressed which was inhibited by quinine. Similar $V_{max}$ values for the expressed uptake of $^{14}$C-TEA (148±4 pmol×oocytes$^{-1}$×h$^{-1}$) and $^3$H-MPP (97±5 pmol×oocytes$^{-1}$×h$^{-1}$) were determined in a sample of oocytes. The existence of polyspecific cation transporters in liver cells has been reported. The uptake of MPP into cultured hepatocytes has recently been measured. In this context, it was found possible to inhibit approximately 90% of the MPP uptake using the same inhibitors which inhibit cation transport expressed by OCT1. The $K_i$ values which were determined for MPP uptake in hepatocytes (O-methylisoprenaline 78 µM, MPP 13 µM, quinine 0.8 µM, decynium 22 0.23 µM and cyanine 863 0.10 µM) were virtually identical to the values which were obtained for the uptake of TEA by the OCT1 protein expressed by Xenopus oocytes. These data suggest that the OCT1 transport protein, or a highly homologous transport protein, is present in the plasma membrane of hepatocytes.

EXAMPLE 5

The nucleotide sequence and the amino acid sequence of OCT1 are depicted in FIG. 2$a_1$A–C (SEQ ID NO.4 and SEQ ID NO.1, respectively). Stop codons and a translation initiation site of the Kozak type (ACGCCATG) are to be found upstream of the open reading frame.

Analysis of the hydrophilicity/hydrophobicity of OCT1 identified 11 hydrophobic α-helical regions which probably traverse the membrane. The hydrophobicity/hydrophilicity indices are presented in FIG. 2b. The putative membrane-spanning regions are from 17 to 27 amino acids in length. They are linked to each other by one long, two medium-length and seven short hydrophilic regions. Since three potential N-glycolisation sites were predicted on the hydrophilic region between the first two membrane-traversing protein regions, the OCT1 orientation depicted in FIG. 2c has been proposed. The first hydrophilic region contains 14 negatively-charged amino acids which can be of importance for the binding of cations to OCT1.

EXAMPLE 6

Various rat tissues and some cell lines were analyzed for the localisation of OCT1 transport protein-specific mRNA using so-called Northern blots. For this purpose, the total RNA was isolated by the the guanidinium/phenol/ chloroform method and the mRNA was purified by means of oligo(dT)-cellulose chromatography. The mRNA was fractionated by formaldehyde agarose gel electrophoresis, transferred to a Hybond-N membrane (Amersham) and then hybridized. For this, 5 µg of mRNA from the rat cells and from the cell line 293, and 1.5 µg of mRNA from the cell lines Caki-1 and LLC-PKI1, were loaded onto the formaldehyde agarose gel. The hybridization was carried out using a $^{32}$P-labeled cDNA fragment of the novel DNA sequence from plasmid pOCT1 (nucleotides 285 to 1196 were used). The hybridization was carried out in hybridization solution (50% formamide, 5×SSPE, 5×Denhardt's solution, 0.5% SDS and 20 µg of salmon sperm DNA) at 42° C. for 18 hours. The membrane was washed in several steps to a final stringency of 0.25×SSPE, 0.1% SDS at 60° C. To display the results for cell line LLC-PK1, the film was exposed for 24 hours, and the film was exposed for 6 hours for the other tracks. An RNA standard (0.14 to 9.5 kilobase range from GIBCO/BRL) was used to determine the size of the RNA fragments. The sizes are given in FIG. 3.

The autoradiograph obtained from the Northern blot analysis is depicted in FIG. 3. Distinct bands at 1.9 kilobases and additional bands at 3.4 and 4.8 kilobases were observed in the case of the renal cortex, the renal medulla, the liver and the intestine. In cell line LLC-PK1, hybridization was only observed in the 3.4 kilobase region. By contrast, no OCT1 signals were observed in renal papilla, in skeletal muscle, in cardiac muscle, in the brain, or in the human embryonic kidney cell line 293 and in Caki-1 cells. Since cardiac and Caki-1 cells contain the extraneuronal noradrenalin transport protein, which is probably identical to the H$^+$ cation antiport protein on luminal kidney membranes, the cation transport proteins in the basolateral and luminal membranes of the proximal renal tubules probably belong to different genetic families. In-situ hybridizations indicated that the OCT1 transport protein is expressed in the proximal renal tubules, in the epithelial cells of the liver and in the enterocytes of the small intestine.

The above examples demonstrate that a novel and unique protein has been cloned which plays an important role in eliminating cationic pharmaceuticals from the kidney and liver. This protein is presumably also involved in the absorption of cationic compounds from the intestine. Although cation transport and the excretion of pharmaceuticals have been intensively investigated for more than 30 years, it has only been possible in the past to make minor advances. The reason for this is that excretion of pharmaceuticals from the liver and kidneys includes transport across the basolateral and the luminal plasma membranes of the epithelial cells and that these transport processes are brought about by functionally different cation transport proteins. In addition to this, the possibility cannot be excluded that different cation transport proteins with similar substrate specificities are present in both the luminal and the basolateral renal membranes. One type of cation transport protein has been identified as a result of cloning the novel OCT1 transport protein. This has opened up many options for further research into the excretion of cationic pharmaceuticals.

EXAMPLE 7

Using the techniques described in the present application, it has been found possible to clone two human genes which are homologous with OCT1 and to sequence them completely or partially, respectively. The completely sequenced gene (HOCT1) is composed of 1885 bases (SEQ ID NO.5) and encodes a protein of 553 amino acids (SEQ ID NO.2). It is depicted in FIG. 2a$_2$A–C. There is 78% identity between the amino acids of OCT1 and HOCT1. The second human gene (HOCT2) is composed of 1896 bases (SEQ ID NO.6)and encodes a protein of 555 amino acids (SEQ ID NO.3). The nucleotide sequence and the deduced amino acid sequence of HOCT2 are depicted in FIG. 2a$_3$A–C. There is 68% identity between the amino acids of OCT1 and HOCT2.

BRIEF DESCRIPTION OF THE DRAWINGS

FIG. 1 shows the expression of OCT1 in Xenopus laevis oocytes. The rates of $^{14}$C-TEA uptake which are indicated represent the mean values of from 10 to 20 measurements ±standard deviation.

FIG. 2a$_2$A–C shows the nucleotide (SEQ ID NO.5) and amino acid (SEQ ID NO.2) sequences of an homologous human kidney gene (HOCT1). The gene fragment which is depicted encompasses 1885 bases and encodes 553 amino acids.

FIG. $2a_3$A–C shows a nucleotide sequence (SEQ ID NO.6) and an amino acid sequence (SEQ ID NO.3) of a second homologous human kidney gene (HOCT2). The gene fragment depicted encompasses 1856 bases and encodes 555 amino acids.

Figure 1A:
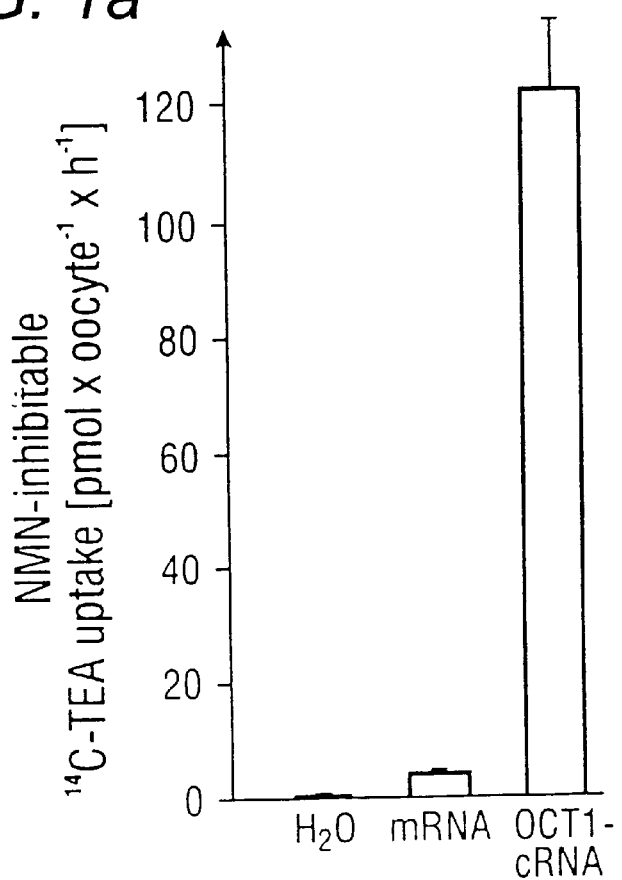
FIG. 1a shows a comparison of the NMN-inhibited uptake of $^{14}$C-TEA which was observed after injecting water, 20 ng of rat kidney mRNA or 10 ng of OCT1 cRNA. The concentrations of $^{14}$C-TEA and NMN in the incubation media were 200 µM and 10 mM, respectively.
Figure 1B:
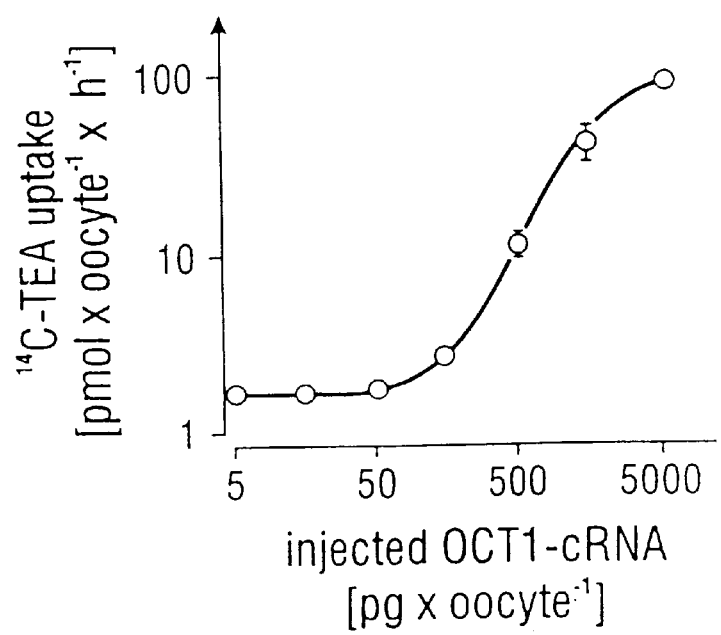
FIG. 1b shows the rates of uptake of 200 µM $^{14}$C-TEA after injecting different quantities of OCT1 cRNA. The curve was computed after fitting the Hill equation to the resulting data (n=1.9±0.2).
Figure 1C:
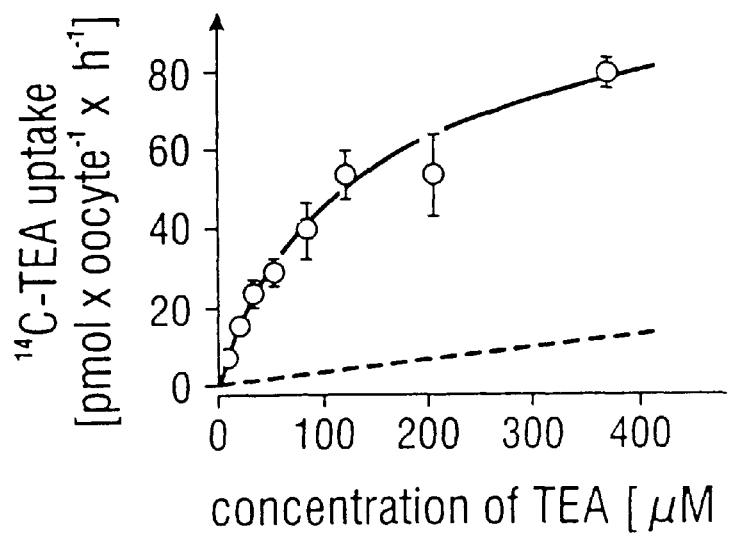
FIG. 1c shows the substrate-dependence of the $^{14}$C-TEA uptake which was expressed following the injection of 3 ng of OCT1 cRNA per oocyte. The continuous line shows the total uptake which contains a saturable component and a linear component which was determined in control oocytes injected with water. The linear component was fitted by means of linear regression (dashed line, 30 fmol×h$^{-1}$× oocyte$^{-1}$×µM$^{-1}$). The saturable component was fitted using the Michaelis Menten equation (K$_m$ 95±10 µM, V$_{max}$ 81±5 pmol×h$^{-1}$×oocyte$^{-1}$). The unbroken line was computed by fitting to an equation which contains both components.
Figure 1D:
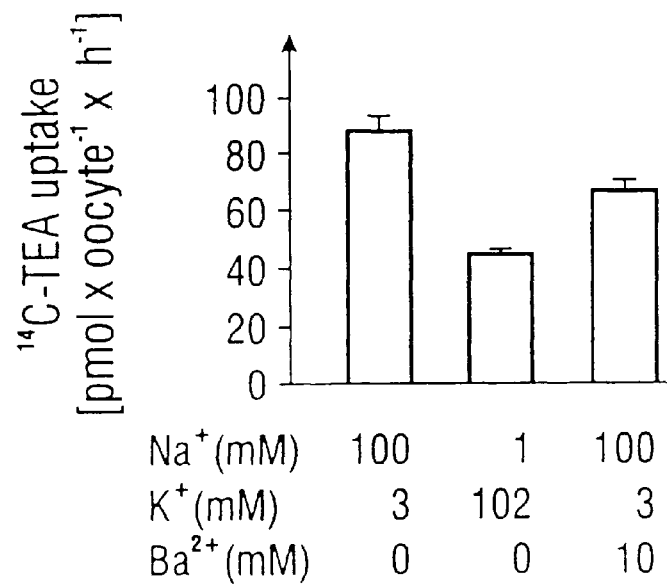
FIG. 1d shows the dependence on potential of the $^{14}$C-TEA uptake in oocytes which were injected with 3 ng of OCT1 cRNA. The uptake of 95 µM $^{14}$C-TEA was measured in the presence of the given concentrations of Na$^+$, K$^+$ and Ba$^{2+}$. Under these conditions, the membrane potentials were between –40 and –60 mV (100 mM Na$^+$ and 3 mM K$^+$), from 0 to –10 mV (1 mM Na$^+$ and 102 mM K+) and between –18 and –22 mV (100 mM Na$^+$, 3 mM K$^+$ $^{and}$ 10 mM Ba$^{2+}$).
Figure 1E:
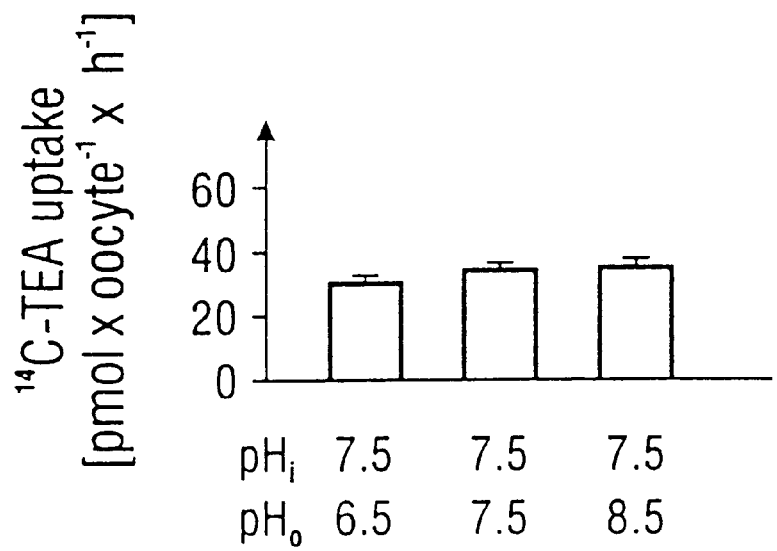
FIG. 1e shows the uptake of 95 µM $^{14}$C-TEA in the presence and absence of proton gradients in oocytes which were injected with 3 ng of OCT1-cRNA. In order to prevent proton gradient-induced changes in the membrane potential, which would alter the uptake of $^{14}$C-TEA, the measurements were carried out in the presence of 102 mM K$^+$ and 1 mM Na$^+$ in the incubation medium. This resulted in the membrane potential being brought to approximately 0 mV. pH measurements using microelectrodes indicated that the pH changed by less than 0.1 unit during the 30-minute uptake period.
Figure 1F:
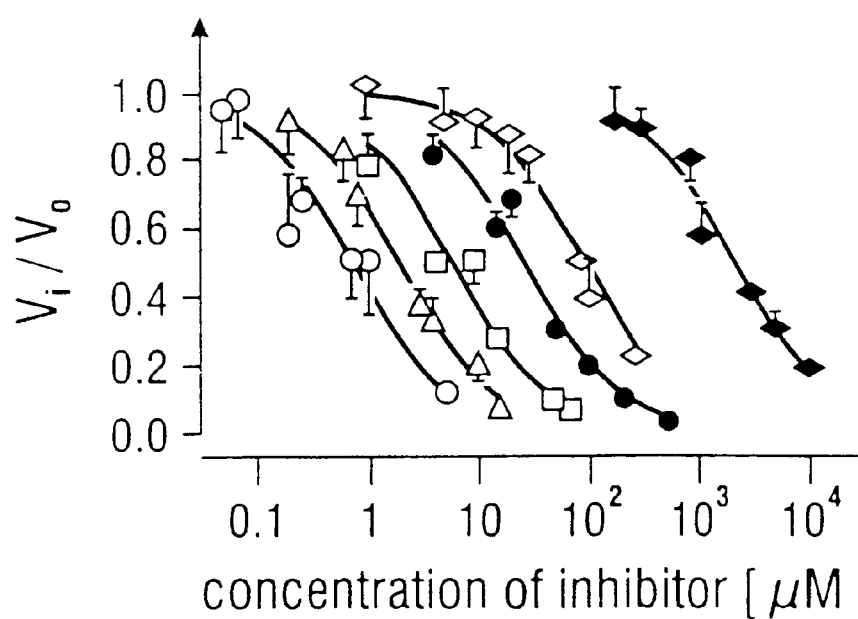
FIG. 1f shows the inhibition of OCT1-elicited $^{14}$C-TEA uptake by decynium 22 (○), quinine (Δ), desipramine (□), procainamide (●), O-methylisoprenaline (◇) and tetramethylammonium (◆). The oocytes were injected with 5 ng of OCT1-cRNA and the measurements were carried out using 95 µM $^{14}$C-TEA.
Figure 2B:
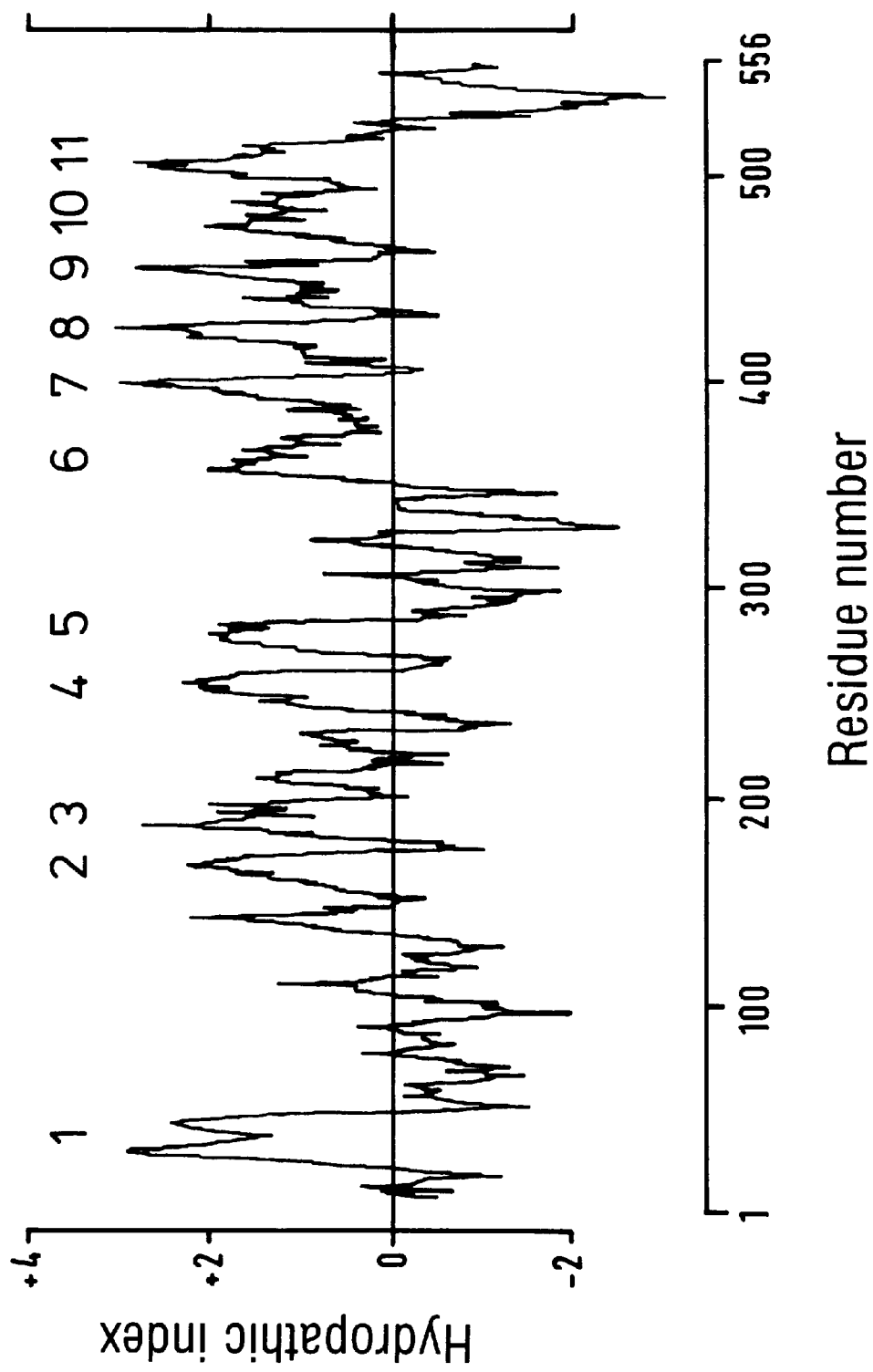
FIG. 2a$_1$A–C shows the nucleotide sequence of OCT1 (SEQ ID NO.4) and the amino acid sequence (SEQ ID NO.1) deduced from it. The putative transmembrane regions have been underlined and potential N-glycosylation sites of the NXT/S type are indicated by asterisks.

FIG. 2b shows a Kyte/Doolittle hydrophobicity/hydrophilicity analysis of OCT1 using a window of 9 amino acids. The putative transmembrane regions are numbered 1 to 11.

Figure 2C:
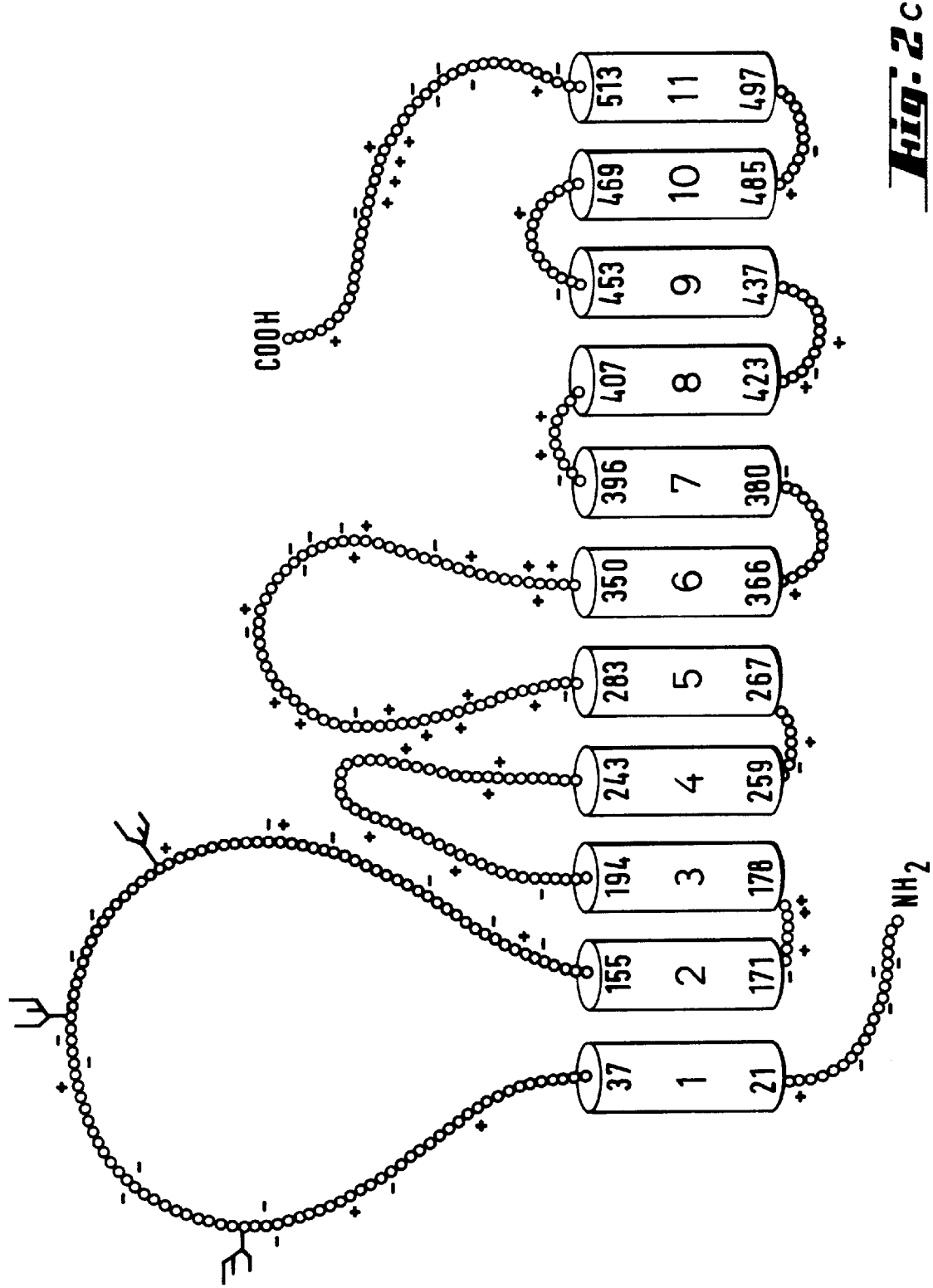

FIG. 2c shows a diagrammatic representation of OCT1. The amino acid residues Arg, Lys and His are indicated by plus signs and the amino acid residues Glu and Asp by minus signs. Potential glycosylation sites in the first hydrophilic loop have been identified.

FIG. 3 shows the location of OCT1-specific mRNA in various rat tissues and in some cell lines.

We claim:

1. An epithelial cell line which constantly expresses a transport protein, wherein said transport protein transports either or both of cationic xenobiotics and pharmaceuticals from blood into liver or kidney epithelial cells, or transports either or both of cationic xenobiotics and pharmaceuticals from the intestine into the blood circulation, said transport protein comprising a sequence of amino acids selected from the amino acid sequences shown in FIGS. $2a_1$ (SEQ ID NO. 1), FIG. $2a_2$ (SEQ ID NO. 2), or FIG. $2a_3$ (SEQ ID NO. 3).

2. A composition of matter comprising an epithelial cell line as claimed in claim 1 and a buffer.

3. A isolated DNA sequence encoding a transport protein, wherein said transport protein transports either or both of cationic xenobiotics and pharmaceuticals from blood into liver or kidney epithelial cells, or transports either or both of cationic xenobiotics and pharmaceuticals from the intestine into the blood circulation, said transport protein comprising a sequence of amino acids selected from the amino acid sequences shown in FIGS. $2a_1$ (SEQ ID NO. 1), FIG. $2a_2$ (SEQ ID NO. 2), or FIG. $2a_3$ (SEQ ID NO. 3).

4. A vector comprising the isolated DNA sequence of claim 3.

5. A host cell comprising the vector of claim 4.

6. A isolated DNA sequence comprising a sequence of at least 21 contiguous nucleotides selected from the DNA sequences shown in FIGS. $2a_1$ (SEQ ID NO. 4), FIG. $2a_2$ (SEQ ID NO. 5), or FIG. $2a_3$ (SEQ ID NO. 6).

7. The isolated DNA sequence as claimed in claim 6, wherein said sequence comprises at least 30 contiguous nucleotides selected from the DNA sequences shown in FIGS. $2a_1$A–C (SEQ ID NO. 4), FIG. $2a_2$A–C (SEQ ID NO. 5), or FIG. $2a_3$A–C (SEQ ID NO. 6).

8. The isolated DNA sequence as claimed in claim 6, wherein said sequence comprises at least 42 contiguous nucleotides selected from the DNA sequences shown in FIGS. $2a_1$A–C (SEQ ID NO. 4), FIG. $2a_2$A–C (SEQ ID NO. 5), or FIG. $2a_3$A–C (SEQ ID NO. 6).

9. A vector comprising the isolated DNA sequence of claim 6.

10. A host cell comprising the vector of claim 9.

11. A process for preparing an epithelial cell line which constantly expresses a transport protein comprising a sequence of amino acids selected from the amino acid sequences shown in FIGS. $2a_1$A–C (SEQ ID NO. 1), FIG. $2a_2$A–C (SEQ ID NO. 2), or FIG. $2a_3$A–C (SEQ ID NO. 3), wherein said transport protein transports either or both of cationic xenobiotics and pharmaceuticals from blood into liver or kidney epithelial cells, or transports either or both of cationic xenobiotics and pharmaceuticals from the intestine into the blood circulation, comprising:
(a) constructing a isolated DNA by incorporating a DNA sequence encoding said transport protein into a vector; and
(b) transforming said isolated DNA into an epithelial cell line which prior to said transformation does not express said transport protein.

12. An epithelial cell line made according to the process of claim 11.

13. A isolated DNA sequence that hybridizes to the DNA sequences shown in FIGS. $2a_1$A–C (SEQ ID NO. 4), FIG. $2a_2$A–C (SEQ ID NO. 5), or FIG. $2a_3$A–C (SEQ NO. 6), or to their complementary DNA sequences, wherein said recombinant DNA sequence hybridizes at 42° C. in a hybridization solution comprising 50% formamide, 5× SSPE, 5× Denhardt's solution and 0.5% SDS.

14. A isolated DNA sequence encoding a transport protein, wherein said transport protein transports either or both of cationic xenobiotics and pharmaceuticals from blood into liver or kidney epithelial cells, or transports either or both of cationic xenobiotics and pharmaceuticals from the intestine into the blood circulation, comprising any of the DNA sequences depicted in FIGS. $2a_1$A–C (SEQ ID NO. 4), FIG. $2a_2$A–C (SEQ ID NO. 5), or FIG. $2a_3$A–C (SEQ ID NO. 6).

15. A vector comprising the isolated DNA sequence of claim 14.

16. A host cell comprising the vector of claim 15.

17. A isolated DNA sequence comprising:
(a) nucleotides encoding amino acids 20–46, 154–171, 178–197, 243–260, 267–283, 350–366, 380–398, 406–425, 435–452, 469–485 or 494–514 as depicted in FIG. $2a_1$A–C (SEQ ID NO. 1);
(b) nucleotides encoding amino acids 20–46, 153–170, 177–196, 242–259, 266–282, 349–365, 379–397, 405–424, 433–450, 467–483 or 492–512 as depicted in FIG. $2a_2$A–C (SEQ ID NO. 2); or
(c) nucleotides encoding amino acids 21–47, 154–171, 243–260, 267–283, 349–366, 380–398, 406–425, 435–452, 469–485 or 494–514 as depicted in FIG. $2a_3$A–C (SEQ ID NO. 3).

18. A vector comprising the isolated DNA sequence of claim 17.

19. A host cell comprising the vector of claim 18.

20. A isolated DNA sequence comprising nucleotides 42–51, 59–64, 86–93, 137–142, 146–165, 206–213, 224–231, 246–252, 316–334, 372–381, 410–417, 437–447, 454–462, 491–498, 548–570, 673–681, 900–907, 1090–1096, 1111–1116, 1124–1130, 1164–1173, 1208–1215, 1224–1230, 1232–1237, 1280–1290, 1388–1395, 1400–1413, 1415–1420 or 1555–1562 as depicted in FIG. $2a_1$A–C (SEQ ID NO. 4).

21. A vector comprising the isolated DNA sequence of claim 20.

22. A host cell comprising the vector of claim 21.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 556 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

```
Met Pro Thr Val Asp Asp Val Leu Glu Gln Val Gly Glu Phe Gly Trp
 1               5                  10                  15

Phe Gln Lys Gln Ala Phe Leu Leu Cys Leu Ile Ser Ala Ser Leu
                20                  25                  30

Ala Pro Ile Tyr Val Gly Ile Val Phe Leu Gly Phe Thr Pro Gly His
            35                  40                  45

Tyr Cys Gln Asn Pro Gly Val Ala Glu Leu Ser Gln Arg Cys Gly Trp
        50                  55                  60

Ser Gln Ala Glu Glu Leu Asn Tyr Thr Val Pro Gly Leu Gly Pro Ser
65                  70                  75                  80

Asp Glu Ala Ser Phe Leu Ser Gln Cys Met Arg Tyr Glu Val Asp Trp
                85                  90                  95

Asn Gln Ser Thr Leu Asp Cys Val Asp Pro Leu Ser Ser Leu Val Ala
                100                 105                 110

Asn Arg Ser Gln Leu Pro Leu Gly Pro Cys Glu His Gly Trp Val Tyr
            115                 120                 125

Asp Thr Pro Gly Ser Ser Ile Val Thr Glu Phe Asn Leu Val Cys Gly
        130                 135                 140

Asp Ala Trp Lys Val Asp Leu Phe Gln Ser Cys Val Asn Leu Gly Phe
145                 150                 155                 160

Phe Leu Gly Ser Leu Val Val Gly Tyr Ile Ala Asp Arg Phe Gly Arg
                165                 170                 175

Lys Leu Cys Leu Leu Val Thr Thr Leu Val Thr Ser Val Ser Gly Val
            180                 185                 190

Leu Thr Ala Val Ala Pro Asp Tyr Thr Ser Met Leu Leu Phe Arg Leu
        195                 200                 205

Leu Gln Gly Met Val Ser Lys Gly Ser Trp Val Ser Gly Tyr Thr Leu
        210                 215                 220

Ile Thr Glu Phe Val Gly Ser Gly Tyr Arg Arg Thr Thr Ala Ile Leu
225                 230                 235                 240
```

```
Tyr Gln Met Ala Phe Thr Val Gly Leu Val Gly Leu Ala Gly Val Ala
                245                 250                 255
Tyr Ala Ile Pro Asp Trp Arg Trp Leu Gln Leu Ala Val Ser Leu Pro
                260                 265                 270
Thr Phe Leu Phe Leu Leu Tyr Tyr Trp Phe Val Pro Glu Ser Pro Arg
                275                 280                 285
Trp Leu Leu Ser Gln Lys Arg Thr Thr Arg Ala Val Arg Ile Met Glu
    290                 295                 300
Gln Ile Ala Gln Lys Asn Gly Lys Val Pro Pro Ala Asp Leu Lys Met
305                 310                 315                 320
Leu Cys Leu Glu Glu Asp Ala Ser Glu Lys Arg Ser Pro Ser Phe Ala
                325                 330                 335
Asp Leu Phe Arg Thr Pro Asn Leu Arg Lys His Thr Val Ile Leu Met
                340                 345                 350
Tyr Leu Trp Phe Ser Cys Ala Val Leu Tyr Gln Gly Leu Ile Met His
                355                 360                 365
Val Gly Ala Thr Gly Ala Asn Leu Tyr Leu Asp Phe Phe Tyr Ser Ser
    370                 375                 380
Leu Val Glu Phe Pro Ala Ala Phe Ile Ile Leu Val Thr Ile Asp Arg
385                 390                 395                 400
Ile Gly Arg Ile Tyr Pro Ile Ala Ala Ser Asn Leu Val Thr Gly Ala
                405                 410                 415
Ala Cys Leu Leu Met Ile Phe Ile Pro His Glu Leu His Trp Leu Asn
                420                 425                 430
Val Thr Leu Ala Cys Leu Gly Arg Met Gly Ala Thr Ile Val Leu Glu
    435                 440                 445
Met Val Cys Leu Val Asn Ala Glu Leu Tyr Pro Thr Phe Ile Arg Asn
    450                 455                 460
Leu Gly Met Met Val Cys Ser Ala Leu Cys Asp Leu Gly Gly Ile Phe
465                 470                 475                 480
Thr Pro Phe Met Val Phe Arg Leu Met Glu Val Trp Gln Ala Leu Pro
                485                 490                 495
Leu Ile Leu Phe Gly Val Leu Gly Leu Thr Ala Gly Ala Met Thr Leu
                500                 505                 510
Leu Leu Pro Glu Thr Lys Gly Val Ala Leu Pro Glu Thr Ile Glu Glu
                515                 520                 525
Ala Glu Asn Leu Gly Arg Arg Lys Ser Lys Ala Lys Glu Asn Thr Ile
                530                 535                 540
Tyr Leu Gln Val Gln Thr Gly Lys Ser Ser Thr
545                 550                 555
```

(2) INFORMATION FOR SEQ ID NO:2:

(i) SEQUENCE CHARACTERISTICS:
        (A) LENGTH: 553 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

```
Met Pro Thr Val Asp Asp Ile Leu Glu Gln Val Gly Glu Ser Gly Trp
1               5                   10                  15
Phe Gln Lys Gln Ala Phe Leu Ile Leu Cys Leu Leu Ser Ala Ala Phe
                20                  25                  30
```

-continued

```
Ala Pro Ile Cys Val Gly Ile Val Phe Leu Gly Phe Thr Pro Asp His
        35                  40                  45
His Cys Gln Ser Pro Gly Val Ala Glu Leu Ser Gln Arg Cys Gly Trp
 50                  55                  60
Ser Pro Ala Glu Glu Leu Asn Tyr Thr Val Pro Gly Leu Gly Pro Ala
 65                  70                  75                  80
Gly Glu Ala Phe Leu Gly Gln Cys Arg Arg Tyr Glu Val Asp Trp Asn
                 85                  90                  95
Gln Ser Ala Leu Ser Cys Val Asp Pro Leu Ala Ser Leu Ala Thr Asn
                100                 105                 110
Arg Ser His Leu Pro Leu Gly Pro Cys Gln Asp Gly Trp Val Tyr Asp
        115                 120                 125
Thr Pro Gly Ser Ser Ile Val Thr Glu Phe Asn Leu Val Cys Ala Asp
        130                 135                 140
Ser Trp Lys Leu Asp Leu Phe Gln Ser Cys Leu Asn Ala Gly Phe Phe
145                 150                 155                 160
Phe Gly Ser Leu Gly Val Gly Tyr Phe Ala Asp Arg Phe Gly Arg Lys
                165                 170                 175
Leu Cys Leu Leu Gly Thr Val Leu Val Asn Ala Val Ser Gly Val Leu
                180                 185                 190
Met Ala Phe Ser Pro Asn Tyr Met Ser Met Leu Leu Phe Arg Leu Leu
        195                 200                 205
Gln Gly Leu Val Ser Lys Gly Asn Trp Met Ala Gly Tyr Thr Leu Ile
        210                 215                 220
Thr Glu Phe Val Gly Ser Gly Ser Arg Arg Thr Val Ala Ile Met Tyr
225                 230                 235                 240
Gln Met Ala Phe Thr Val Gly Leu Val Ala Leu Thr Gly Leu Ala Tyr
                245                 250                 255
Ala Leu Pro His Trp Arg Trp Leu Gln Leu Ala Val Ser Leu Pro Thr
                260                 265                 270
Phe Leu Phe Leu Leu Tyr Tyr Trp Cys Val Pro Glu Ser Pro Arg Trp
        275                 280                 285
Leu Leu Ser Gln Lys Arg Asn Thr Glu Ala Ile Lys Ile Met Asp His
        290                 295                 300
Ile Ala Gln Lys Asn Gly Lys Leu Pro Pro Ala Asp Leu Lys Met Leu
305                 310                 315                 320
Ser Leu Glu Glu Asp Val Thr Glu Lys Leu Ser Pro Ser Phe Ala Asp
                325                 330                 335
Leu Phe Arg Thr Pro Arg Leu Arg Lys Arg Thr Phe Ile Leu Met Tyr
                340                 345                 350
Leu Trp Phe Thr Asp Ser Val Leu Tyr Gln Gly Leu Ile Leu His Met
        355                 360                 365
Gly Ala Thr Ser Gly Asn Leu Tyr Leu Asp Phe Leu Tyr Ser Ala Leu
        370                 375                 380
Val Glu Ile Pro Gly Ala Phe Ile Ala Leu Ile Thr Ile Asp Arg Val
385                 390                 395                 400
Gly Arg Ile Tyr Pro Met Ala Val Ser Asn Leu Leu Ala Gly Ala Ala
                405                 410                 415
Cys Leu Val Ile Phe Ile Ser Pro Asp Leu His Trp Leu Asn Ile Ile
                420                 425                 430
Ile Met Cys Val Gly Arg Met Gly Ile Thr Ile Ala Ile Gln Met Ile
        435                 440                 445
Cys Leu Val Asn Ala Glu Leu Tyr Pro Thr Phe Val Arg Asn Leu Arg
```

```
              450                 455                 460
    Val Met Val Cys Ser Ser Leu Cys Asp Ile Gly Ile Ile Thr Pro
    465                 470                 475                 480

Phe Ile Val Phe Arg Leu Arg Glu Val Trp Gln Ala Leu Pro Leu Ile
                    485                 490                 495

Leu Phe Ala Val Leu Gly Leu Leu Ala Ala Gly Val Thr Leu Leu Leu
                    500                 505                 510

Pro Glu Thr Lys Gly Asp Ala Leu Pro Glu Thr Met Lys Asp Ala Glu
                    515                 520                 525

Asn Leu Gly Arg Lys Ala Lys Pro Lys Glu Asn Thr Ile Tyr Leu Lys
                    530                 535                 540

Val Gln Thr Ser Glu Pro Ser Gly Thr
    545                 550
```

(2) INFORMATION FOR SEQ ID NO:3:

(i) SEQUENCE CHARACTERISTICS:
        (A) LENGTH: 555 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
    Met Pro Thr Thr Val Asp Asp Val Leu Glu His Gly Gly Glu Phe His
    1                   5                   10                  15

Phe Phe Gln Lys Gln Met Phe Leu Leu Ala Leu Leu Ser Ala Thr
                    20                  25                  30

Phe Ala Pro Ile Tyr Val Gly Ile Val Phe Leu Gly Phe Thr Pro Asp
                    35                  40                  45

His Arg Cys Arg Ser Pro Gly Val Ala Glu Leu Ser Leu Arg Cys Gly
                    50                  55                  60

Trp Ser Pro Ala Glu Glu Leu Asn Tyr Thr Val Pro Gly Pro Gly Pro
    65                  70                  75                  80

Ala Gly Glu Ala Ser Pro Arg Gln Cys Arg Arg Tyr Glu Val Asp Trp
                    85                  90                  95

Asn Gln Ser Thr Phe Asp Cys Val Asp Pro Leu Ala Ser Leu Asp Thr
                    100                 105                 110

Asn Arg Ser Arg Leu Pro Leu Gly Pro Cys Arg Asp Gly Trp Val Tyr
                    115                 120                 125

Glu Thr Pro Gly Ser Ser Ile Val Thr Glu Phe Asn Leu Val Cys Ala
    130                 135                 140

Asn Ser Trp Met Leu Asp Leu Phe Gln Ser Ser Val Asn Val Gly Phe
    145                 150                 155                 160

Phe Ile Gly Ser Met Ser Ile Gly Tyr Ile Ala Asp Arg Phe Gly Arg
                    165                 170                 175

Lys Leu Cys Leu Leu Thr Thr Val Leu Ile Asn Ala Ala Ala Gly Val
                    180                 185                 190

Leu Met Ala Ile Ser Pro Thr Tyr Thr Trp Met Leu Ile Phe Arg Leu
                    195                 200                 205

Ile Gln Gly Leu Val Ser Lys Ala Gly Trp Leu Ile Gly Tyr Ile Leu
                    210                 215                 220

Ile Thr Glu Phe Val Gly Gly Arg Tyr Arg Arg Thr Val Gly Ile Phe
    225                 230                 235                 240

Tyr Gln Val Ala Tyr Thr Val Gly Leu Leu Val Leu Ala Gly Val Ala
```

```
            245                 250                 255
    Tyr Ala Leu Pro His Trp Arg Trp Leu Gln Phe Thr Val Ala Leu Pro
                260                 265                 270

Asn Phe Phe Leu Leu Tyr Tyr Trp Cys Ile Pro Glu Ser Pro Arg
            275                 280                 285

Trp Leu Ile Ser Gln Asn Lys Asn Ala Glu Ala Met Arg Ile Ile Lys
        290                 295                 300

His Ile Ala Lys Lys Asn Gly Lys Ser Leu Pro Ala Ser Leu Gln Arg
    305                 310                 315                 320

Leu Arg Leu Glu Glu Thr Gly Lys Lys Leu Asn Pro Ser Phe Leu
                325                 330                 335

Asp Leu Val Arg Thr Pro Gln Ile Arg Lys His Thr Met Ile Leu Met
                340                 345                 350

Tyr Asn Trp Phe Thr Ser Ser Val Leu Tyr Gln Gly Leu Ile Met His
                355                 360                 365

Met Gly Leu Ala Gly Asp Asn Ile Tyr Leu Asp Phe Phe Tyr Ser Ala
                370                 375                 380

Leu Val Glu Phe Pro Ala Ala Phe Met Ile Ile Leu Ile Ile Asp Arg
    385                 390                 395                 400

Ile Gly Arg Arg Tyr Pro Trp Ala Ala Ser Asn Met Val Ala Gly Ala
                405                 410                 415

Ala Cys Leu Ala Ser Val Phe Ile Pro Gly Asp Leu Gln Trp Leu Lys
                420                 425                 430

Ile Ile Ile Ser Cys Leu Gly Arg Met Gly Ile Thr Met Ala Tyr Glu
                435                 440                 445

Ile Val Cys Leu Val Asn Ala Glu Leu Tyr Pro Thr Phe Ile Arg Asn
                450                 455                 460

Leu Gly Val His Ile Cys Ser Ser Met Cys Asp Ile Gly Gly Ile Ile
    465                 470                 475                 480

Thr Pro Phe Leu Val Tyr Arg Leu Thr Asn Ile Trp Leu Glu Leu Pro
                485                 490                 495

Leu Met Val Phe Gly Val Leu Gly Val Ala Gly Gly Leu Ala Leu
                500                 505                 510

Leu Leu Pro Glu Thr Lys Gly Lys Ala Leu Pro Glu Thr Ile Glu Glu
                515                 520                 525

Ala Glu Asn Met Gln Arg Pro Arg Lys Asn Lys Glu Lys Met Ile Tyr
                530                 535                 540

Leu Gln Val Gln Lys Leu Asp Ile Pro Leu Asn
    545                 550                 555

(2) INFORMATION FOR SEQ ID NO:4:

(i) SEQUENCE CHARACTERISTICS:
         (A) LENGTH: 1882 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:4:

GCAGGCCTGG CTAAACTGGT GAGGGCCCTA CCCAGCCATG CCCACCGTGG ATGATGTCCT      60

GGAGCAAGTT GGAGAGTTTG GCTGGTTCCA GAAACAAGCC TTCCTGTTGC TATGCCTGAT     120

CTCAGCTTCT TTAGCTCCCA TCTATGTGGG CATCGTCTTC CTGGGCTTCA CCCCTGGACA     180

TTATTGCCAG AATCCTGGGG TGGCTGAGCT GAGCCAGCGG TGTGGCTGGA GCCAGGCAGA     240
```

```
GGAGCTGAAC TACACTGTGC CGGGCCTGGG ACCTTCGGAC GAGGCCTCCT TCCTCAGCCA     300

GTGCATGAGG TATGAGGTGG ACTGGAACCA GAGCACCCTT GACTGTGTGG ACCCACTGTC     360

CAGCCTGGTT GCCAACAGGA GTCAGTTGCC ATTGGGCCCC TGCGAGCATG GCTGGGTATA     420

CGACACTCCC GGCTCCTCCA TCGTCACTGA GTTTAACCTG GTGTGTGGAG ACGCCTGGAA     480

AGTGGACCTT TTTCAGTCCT GTGTGAACTT GGGCTTCTTC CTGGGCTCCC TGGTTGTGGG     540

TTACATTGCA GACAGGTTTG GCCGTAAGCT CTGTCTCTTG GTGACCACGC TGGTCACATC     600

TGTGTCCGGT GTGCTAACAG CGGTGGCCCC AGACTATACA TCCATGTTGC TCTTTCGCCT     660

GCTGCAGGGC ATGGTCAGCA AGGGCAGCTG GGTGTCCGGC TATACCTTGA TCACAGAGTT     720

TGTCGGCTCT GGCTACAGGA GAACGACGGC CATTTTGTAC CAGATGGCCT TCACAGTGGG     780

GCTAGTGGGG CTTGCCGGGG TGGCCTATGC CATTCCAGAC TGGCGCTGGC TCCAGCTAGC     840

TGTGTCCCTG CCTACCTTCC TCTTCCTGCT GTATTACTGG TTTGTCCCAG AATCCCCCCG     900

GTGGCTGTTG TCCCAGAAGA GAACCACGCG AGCTGTCAGG ATAATGGAGC AAATTGCACA     960

GAAGAACGGG AAGGTGCCTC CTGCTGACCT GAAGATGCTC TGCCTTGAGG AGGATGCCTC    1020

AGAAAAGCGA AGTCCTTCGT TGCCGACCT GTTCCGCACT CCCAACCTGA GGAAGCACAC    1080

CGTCATCCTG ATGTATCTAT GGTTCTCTTG TGCTGTGCTG TACCAGGGTC TCATCATGCA    1140

CGTGGGAGCC ACAGGGCCA ACCTCTACCT GGACTTCTTT TATTCTTCTC TGGTGGAATT    1200

CCCCGCGGCC TTCATCATCC TGGTCACCAT TGACCGCATT GGCCGCATCT ACCCAATAGC    1260

GGCCTCGAAT CTGGTGACGG GGGCAGCCTG CCTCCTCATG ATCTTTATCC CGCATGAGCT    1320

GCACTGGTTG AACGTTACCC TCGCCTGTCT TGGCCGTATG GGGGCCACCA TTGTGCTGCA    1380

GATGGTCTGC CTGGTGAACG CTGAGCTGTA CCCTACATTC ATCAGGAATC TTGGGATGAT    1440

GGATTGCTCT GCCCTGTGTG ACCTGGGTGG GATCTTCACC CCCTTCATGG TGTTCAGGCT    1500

GATGGAAGTT TGGCAAGCCC TGCCCCTCAT TTTGTTTGGG GTTTTGGGCC TGACTGCTGG    1560

GGCCATGACT CTTCTTCTCC CAGAGACCAA GGGTGTGGCT TTGCCTGAGA CTATTGAAGA    1620

AGCAGAGAAC CTGGGGAGGA GGAAATCAAA GGCCAAAGAA AACACGATTT ACCTTCAGGT    1680

CCAAACAGGC AAGTCCTCAA GTACCTGACA GGGATGCTGT GCCAGGAGCT GAGTGGCAGA    1740

GAGAAAGGAG GACTTGCCAC TTGGAGGATT CCCAGAAGCC TTTGCCTTTC CAGACTCTTG    1800

TATATATGCA CCAGGTTCCA AATGAACTAC CAACCTTAAA GACTTTTCTG AAAGCCCAAA    1860

AAAAAAAAAA AAAAAAAAA AA                                             1882
```

(2) INFORMATION FOR SEQ ID NO:5:

(i) SEQUENCE CHARACTERISTICS:
        (A) LENGTH: 1885 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
GAGGGAGACA TTGCACCTGG CCACTGCAGC CCAGAGCAGG TCTGGCCACG GCCATGAGCA      60

TGCTGAGCCA TCATGCCCAC CGTGGATGAC ATTCTGGAGC AGGTTGGGGA GTCTGGCTGG     120

TTCCAGAAGC AAGCCTTCCT CATCTTATGC CTGCTGTCGG CTGCCTTTGC GCCCATCTGT     180

GTGGGCATCG TCTTCCTGGG TTTCACACCT GACCACCACT GCCAGAGCCC TGGGGTGGCT     240

GAGCTGAGCC AGCGCTGTGG CTGGAGCCCT GCGGAGGAGC TGAACTATAC AGTGCCAGGC     300
```

-continued

```
CTGGGGCCCG CGGGCGAGGC CTTCCTTGGC CAGTGCAGGC GCTATGAAGT GGACTGGAAC      360

CAGAGCGCCC TCAGCTGTGT AGACCCCCTG GCTAGCCTGG CCACCAACAG GAGCCACCTG      420

CCGCTGGGTC CCTGCCAGGA TGGCTGGGTG TATGACACGC CCGGCTCTTC CATCGTCACT      480

GAGTTCAACC TGGTGTGTGC TGACTCCTGG AAGCTGGACC TCTTTCAGTC CTGTTTGAAT      540

GCGGGCTTCT TCTTTGGCTC TCTCGGTGTT GGCTACTTTG CAGACAGGTT TGGCCGTAAG      600

CTGTGTCTCC TGGGAACTGT GCTGGTCAAC GCGGTGTCGG GCGTGCTCAT GGCCTTCTCG      660

CCCAACTACA TGTCCATGCT GCTCTTCCGC CTGCTGCAGG GCCTGGTCAG CAAGGGCAAC      720

TGGATGGCTG GCTACACCCT AATCACAGAA TTTGTTGGCT CGGGCTCCAG AAGAACGGTG      780

GCGATCATGT ACCAGATGGC CTTCACGGTG GGGCTGGTGG CGCTTACCGG GCTGGCCTAC      840

GCCCTGCCTC ACTGGCGCTG GCTGCAGCTG GCAGTCTCCC TGCCCACCTT CCTCTTCCTG      900

CTCTACTACT GGTGTGTGCC GGAGTCCCCT CGGTGGCTGT TATCACAAAA AAGAAACACT      960

GAAGCAATAA AGATAATGGA CCACATCGCT CAAAAGAATG GGAAGTTGCC TCCTGCTGAT     1020

TTAAAGATGC TTTCCCTCGA AGAGGATGTC ACCGAAAAGC TGAGCCCTTC ATTTGCAGAC     1080

CTGTTCCGCA CGCCGCGCCT GAGGAAGCGC ACCTTCATCC TGATGTACCT GTGGTTCACG     1140

GACTCTGTGC TCTATCAGGG GCTCATCCTG CACATGGGCG CCACCAGCGG GAACCTCTAC     1200

CTGGATTTCC TTTACTCCGC TCTGGTCGAA ATCCCGGGGG CCTTCATAGC CCTCATCACC     1260

ATTGACCGCG TGGGCCGCAT CTACCCCATG GCCGTGTCAA ATTTGTTGGC GGGGGCAGCC     1320

TGCCTCGTCA TTTTTATCTC ACCTGACCTG CACTGGTTAA ACATCATAAT CATGTGTGTT     1380

GGCCGAATGG GAATCACCAT TGCAATACAA ATGATCTGCC TGGTGAATGC TGAGCTGTAC     1440

CCCACATTCG TCAGGAACCT CAGAGTGATG GTGTGTTCCT CCCTGTGTGA CATAGGTGGG     1500

ATAATCACCC CCTTCATAGT CTTCAGGCTG AGGGAGGTCT GGCAAGCCTT GCCCCTCATT     1560

TTGTTTGCGG TGTTGGGCCT GCTTGCCGCG GGAGTGACGC TACTTCTTCC AGAGACCAAG     1620

GGGGACGCTT TGCCAGAGAC CATGAAGGAC GCCGAGAACC TTGGGAGAAA AGCAAAGCCC     1680

AAAGAAAACA CGATTTACCT TAAGGTCCAA ACCTCAGAAC CCTCGGGCAC CTGAGAGAGA     1740

TGTTTTGCGG CGATGTCGTG TTGGAGGGAT GAAGATGGAG TTATCCTCTG CAGAAATTCC     1800

TAGACGCCTT CACTTCTCTG TATTCTTCCT CATACTTGCC TACCCCCAAA TTAATATCAG     1860

TCCTAAAGAA AAAAAAAAA AAAAA                                             1885

(2) INFORMATION FOR SEQ ID NO:6:

(i) SEQUENCE CHARACTERISTICS:
        (A) LENGTH: 1896 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GGCCCTGCCC TGAAGGCTGG TCACTTGCAG AGGTAAACTC CCCTCTTTGA CTTCTGGCCA       60

GGGTTTGTGC TGAGCTGGCT GCAGCCGCTC TCAGCCTCGC TCCGGGCACG TCGGGCAGCC      120

TCGGGCCCTC CTGCCTGCAG GATCATGCCC ACCACCGTGG ACGATGTCCT GGAGCATGGA      180

GGGGAGTTTC ACTTTTTCCA GAAGCAAATG TTTTTCCTCT TGGCTCTGCT CTCGGCTACC      240

TTCGCGCCCA TCTACGTGGG CATCGTCTTC CTGGGCTTCA CCCCTGACCA CCGCTGCCGG      300

AGCCCCGGAG TGGCCGAGCT GAGTCTGCGC TGCGGCTGGA GTCCTGCAGA GGAACTGAAC      360
```

```
-continued

TACACGGTGC CGGGCCCAGG ACCTGCGGGC GAAGCCTCCC CAAGACAGTG TAGGCGCTAC    420

GAGGTGGACT GGAACCAGAG CACCTTTGAC TGCGTGGACC CCCTGGCCAG CCTGGACACC    480

AACAGGAGCC GCCTGCCACT GGGCCCCTGC CGGGACGGCT GGGTGTACGA GACGCCTGGC    540

TCGTCCATCG TCACCGAGTT TAACCTGGTA TGTGCCAACT CCTGGATGTT GGACCTATTC    600

CAGTCATCAG TGAATGTAGG ATTCTTTATT GGCTCTATGA GTATCGGCTA CATAGCAGAC    660

AGGTTTGGCC GTAAGCTCTG CCTCCTAACT ACAGTCCTCA TAAATGCTGC AGCTGGAGTT    720

CTCATGGCCA TTTCCCCAAC CTATACGTGG ATGTTAATTT TTCGCTTAAT CCAAGGACTG    780

GTCAGCAAAG CAGGCTGGTT AATAGGCTAC ATCCTGATTA CAGAATTTGT TGGGGGGAGA    840

TATCGGAGAA CAGTGGGGAT TTTTTACCAA GTTGCCTATA CAGTTGGGCT CCTGGTGCTA    900

GCTGGGGTGG CTTACGCACT TCCTCACTGG AGGTGGTTGC AGTTCACAGT TGCTCTGCCC    960

AACTTCTTCT TCTTGCTCTA TTACTGGTGC ATACCTGAGT CTCCCAGGTG GCTGATCTCC   1020

CAGAATAAGA ATGCTGAAGC CATGAGAATC ATTAAGCACA TCGCAAAGAA AAATGGAAAA   1080

TCTCTACCCG CCTCCCTTCA GCGCCTGAGA CTTGAAGAGG AAACTGGCAA GAAATTGAAC   1140

CCTTCATTTC TTGACTTGGT CAGAACTCCT CAGATAAGGA AACATACTAT GATATTGATG   1200

TACAACTGGT TCACGAGCTC TGTGCTCTAC CAGGGCCTCA TCATGCACAT GGGCCTTGCA   1260

GGTGACAATA TCTACCTGGA TTTCTTCTAC TCTGCCCTGG TTGAATTCCC AGCTGCCTTC   1320

ATGATCATCC TCATTATCGA CCGCATCGGA CGCCGTTACC CTTGGGCTGC ATCAAATATG   1380

GTTGCAGGGG CAGCCTGTCT GGCCTCAGTT TTTATACCTG GTGATCTACA ATGGCTAAAA   1440

ATTATTATCT CATGCTTGGG AAGAATGGGG ATCACAATGG CCTATGAGAT AGTCTGCCTG   1500

GTCAATGCTG AGCTGTACCC CACATTCATT AGGAATCTTG GCGTCCACAT CTGTTCCTCA   1560

ATGTGTGACA TTGGTGGCAT CATCACGCCA TTCCTGGTCT ACCGGCTCAC TAACATCTGG   1620

CTTGAGCTCC CGCTGATGGT TTTCGGCGTA CTTGGCTTGG TTGCTGGAGG TCTGGTGCTG   1680

TTGCTTCCAG AAACTAAAGG GAAAGCTTTG CCTGAGACCA TCGAGGAAGC CGAAAATATG   1740

CAAAGACCAA GAAAAAATAA AGAAAAGATG ATTTACCTCC AAGTTCAGAA ACTAGACATT   1800

CCATTGAACT AAGAAGAGAG ACCGTTGCTG CTGTCATGAC CTAGCTTTAT GGCAGCAAGA   1860

CCAAAAGTAG AAATCCCTGC ACTCATCACA AAGCCC                              1896
```